(12) United States Patent
Zhang et al.

(10) Patent No.: US 9,551,703 B2
(45) Date of Patent: Jan. 24, 2017

(54) HIGH PRECISION QUANTITATIVE ASSAY COMPOSITION AND METHODS OF USE THEREFOR

(75) Inventors: Zhen Zhang, Dayton, MD (US); Daniel W. Chan, Clarksville, MD (US)

(73) Assignee: The Johns Hopkins University, Baltimore, MD (US)

( * ) Notice: Subject to any disclaimer, the term of this patent is extended or adjusted under 35 U.S.C. 154(b) by 1286 days.

(21) Appl. No.: 13/388,978

(22) PCT Filed: Aug. 4, 2010

(86) PCT No.: PCT/US2010/044418
§ 371 (c)(1),
(2), (4) Date: Feb. 3, 2012

(87) PCT Pub. No.: WO2011/017436
PCT Pub. Date: Feb. 10, 2011

(65) Prior Publication Data
US 2012/0142554 A1    Jun. 7, 2012

Related U.S. Application Data

(60) Provisional application No. 61/231,143, filed on Aug. 4, 2009.

(51) Int. Cl.
*G01N 33/543*    (2006.01)
*G01N 33/58*    (2006.01)
*B01J 19/00*    (2006.01)

(52) U.S. Cl.
CPC .......... *G01N 33/543* (2013.01); *B01J 19/0046* (2013.01); *G01N 33/582* (2013.01)

(58) Field of Classification Search
CPC ... G01N 33/543; G01N 33/582; B01J 19/0046
See application file for complete search history.

(56) References Cited

U.S. PATENT DOCUMENTS

| 7,177,486 B2 | 2/2007 | Stewart et al. |
| 2003/0092074 A1* | 5/2003 | Ezaki ............... G01N 33/54366 435/7.9 |

(Continued)

FOREIGN PATENT DOCUMENTS

WO    03027262 A2    4/2003

OTHER PUBLICATIONS

International Preliminary Report on Patentability for International Application No. PCT/US2010/044418 (Feb. 7, 2012).

(Continued)

*Primary Examiner* — Jeremy C Flinders
(74) *Attorney, Agent, or Firm* — Mintz Levin Cohn Ferris Glovsky and Popeo, P.C.; Peter F. Corless; Christopher R. Cowles

(57) ABSTRACT

The invention features compositions and methods that are useful for precisely determining the amount of one or more analytes present in a sample. In one aspect, the invention provides a composition for measuring the abundance of one or more target analytes in a sample, where the composition contains a set of detection units for each analyte fixed to a substrate (e.g., a membrane, bead, filter, chip, polymer-based film or glass slide, or other printable surface), where each detection unit contains a discrete amount of a capture agent that specifically binds the target analyte, and the amount of capturing agent varies over the set to form a concentration gradient.

13 Claims, 17 Drawing Sheets

Capturing agent spotted in N concentration levels in a gradient

Capturing agent spotted in M replicates at each concentration levels

Affinity capturing of target analyte in a given specimen

(56) References Cited

U.S. PATENT DOCUMENTS

2003/0124623 A1* 7/2003 Yager et al. .................. 435/7.5
2005/0014179 A1 1/2005 Karlsson et al.
2008/0014575 A1 1/2008 Nelson

OTHER PUBLICATIONS

International Search Report for International Application No. PCT/US2010/044418 (Apr. 12, 2011).
Written Opinion for International Application No. PCT/US2010/044418 (Apr. 12, 2011).

* cited by examiner

Affinity capturing of target analyte in a given specimen

Binary signal of affinity capturing after digitization using a fixed cutoff value (filled square: positive or 1, hollow square: negative or 0). Proportion of positive signals among M replicates at each spotting concentration level is listed below each replication column.

Proportions of positive signals among M replicates at N spotting concentration level are fitted with a curve which in turn can be used as a measure of analyte concentration in specimen (e.g., distance h at fitted curve value = 0.5).

Horizontal position of fitted curve correlates to concentration of analyte in a given specimen

HIGH PRECISION QUANTITATIVE ASSAY COMPOSITION AND METHODS OF USE THEREFOR

CROSS-REFERENCE TO RELATED APPLICATIONS

This application is a 35 U.S.C. §371 U.S. national entry of International Application PCT/US2010/044418 (WO 2011/017436) having an International filing date of Aug. 4, 2010 which claims the benefit of the following U.S. Provisional Application No. 61/231,143, filed Aug. 4, 2009, the entire contents of which are incorporated herein by reference.

BACKGROUND OF THE INVENTION

Recent advances in human understanding of disease have shown that most, if not all diseases, are associated with changes in biological pathways that involve various genomic and proteomic targets. Changes in the level of expressions and alteration of structures of these molecular targets are often associated with and indicative of the initiation, development, and progress of disease, responses to treatment, or long-term outcomes. Multiplexed assay formats have been recently developed to allow the simultaneous analysis of multiple analytes using a single specimen in a single run using various affinity capturing methods. There are, however, limitations to the current technologies. First, the number of tests that can be simultaneously analyzed is still limited and second, the analytical performances in terms of precision, reproducibility, and usable dynamic range are also limited.

In a complex specimen, the targets for multiplexed affinity capturing are typically present at varying concentrations and often have very different biochemical properties and/or other characteristics. The disparate properties of these targets can result in difficulties in providing one assay with capturing conditions that are appropriate for all capturing agents and target analytes.

Advances in high-density affinity-capturing based technologies, such as protein microarrays, have made it possible to quickly spot tens of thousands of affinity capturing agents on a single array. Fluorescent signals that are theoretically proportional to the abundance of the targets are scanned into images to provide readouts of the relative abundance measurements through software tools. Such technologies have become important research assay platforms for profiling the expression of up to tens of thousands of targets simultaneously. However, with such high density, the individual units of affinity capture provide a relatively small area of contact surface for target capturing which in effect limits the dynamic range of target detection and measurement. Variability in the coupling/printing of capturing agents to this limited surface can also result in the underrepresentation of a particular analyte in the final numerical readouts of signals. Such underrepresentation is compounded by variability in the processing of such assays. These factors reduce the analytical performance of the assays and limit there use in applications (e.g., clinical laboratory tests) that require a high degree of precision, reproducibility, and dynamic range. These issues affect not only high-density microarrays, but also to varying degrees other multiplex assay platforms, such as the beads based Luminex technology or the electrochemiluminescence detection based Mesoscale (MSD) technology.

SUMMARY OF THE INVENTION

The invention features compositions and methods that are useful for precisely determining the amount of one or more analytes present in a sample.

In one aspect, the invention provides a composition for measuring the abundance of one or more target analytes in a sample, where the composition contains a set of detection units for each analyte fixed to a substrate (e.g., a membrane, bead, filter, chip, polymer-based film or glass slide, or other printable surface), where each detection unit contains a discrete amount of a capture agent that specifically binds the target analyte, and the amount of capturing agent varies over the set to form a concentration gradient. In one embodiment, the number of detection units present in the set is sufficient to provide a quantitative read-out of the abundance of the target analyte in the sample based on the aggregation of data of an analyte detected by the individual detection units. In another embodiment, the composition is a microarray, a collection of beads, a 2-dimensional surface, a 3-dimensional surface, or other 2 dimensional or 3-dimensional shape that supports the immobilization of a capture agent by a detection unit. In yet another embodiment, the detection unit is a spot of capture reagent present on a microarray, a single bead, a 2-dimensional surface, a 3-dimensional surface, or other 2 dimensional or 3-dimensional shape that supports the immobilization of a capture agent by a detection unit. In another embodiment, the capture agent is a small compound (e.g., organic, inorganic, biotin, or any other chemical compound), a polypeptide (e.g., an antibody or fragment thereof), a polynucleotide (e.g., NA, RNA, a synthetic nucleobase polymer, or an aptamer), a natural or synthetic particle or nanoparticle (e.g., a carboxylated/oxidized diamond nanoparticle). In another embodiment, the amount of capture agent varies linearly exponentially, or non-linearly between detection units in the set. In another embodiment, the number of detection units within the set is optimized to reduce analytical variability or is optimized to expand the dynamic range of the assay. In another embodiment, the composition contains replicates of each detection unit, such that the replicates each comprise an equivalent amount of capture agent.

In another aspect, the invention provides a method for determining the abundance of one or more target analytes in a sample, the method involving contacting the composition of the current application with a target analyte under conditions sufficient to allow binding of the target analyte to the capture agent, detecting binding, and determining the amount of target analyte present in the sample. In one embodiment, binding is detected by contacting the composition of the current application with a detection agent that binds the target analyte. In another embodiment, the detection agent is a polypeptide or fragment thereof containing a detectable moiety. In another embodiment, the polypeptide is an antibody or fragment thereof. In yet another embodiment, the detection agent is a hybridizable polynucleotide containing a detectable moiety. In still another embodiment, the detectable moiety is a radioactive isotope, magnetic bead, metallic bead, fluorescent dye, or enzyme. In another embodiment, the method provides a numerical read-out of the amount of analyte present in the sample. In another embodiment, the amount of target analyte is determined using a programmable digital computer.

In another aspect, the invention provides a device containing a composition for measuring the abundance of a plurality of target analytes in a sample, where the composition contains a set of detection units for each target analyte fixed to a substrate, where each detection unit contains a discrete amount of a capture agent that specifically binds the target analyte, and the amount of capture agent varies over the set to form a concentration gradient. In one embodiment, the device is a column, a two-dimensional or 3-dimensional surface or shape that supports the immobilization of capturing agents. In another embodiment, the composition contains a multiplicity of beads.

In another aspect, the invention provides a kit containing the composition of the current application or the device of the current application, and written instructions for using the composition or device in any of the methods of the current application.

In another aspect, the invention provides a kit containing the composition of the current application or the device of the current application, and written instructions for using the composition or device in any of the methods of the current application.

In another aspect, the invention provides a method of analyzing the composition of the current application, the method involving for each detection unit, computing a proportion of positive detection units. In one embodiment, the step of computing the proportion of positive detection units includes removing outliers. In another embodiment, the method further involves associating each of the proportions of positive detection units with its corresponding amount of capture agent. In another embodiment, the method further involves utilizing the associated proportions of positive detection units and capture agent amounts to quantify the amount of a target analyte. In another embodiment, the utilizing step includes fitting a curve f(b) to the associated proportions of positive detection units and capture agent amounts. In another embodiment, the curve f(b) is a parametric curve. In another embodiment, the curve f(b) represents a truncated sigmoid function. In another embodiment, the method further involves utilizing the curve to compute a value h, where f(h) equals a constant k. In another embodiment, k=0.5. In another embodiment, a positive detection unit is a unit that exhibits a response exceeding a defined threshold. In another embodiment, the defined threshold is a user-defined threshold. In another embodiment, the response is measured with an imaging device. In another embodiment, the imaging device is a fluorescence imaging device. In another embodiment, the method is a computer-implemented method.

In another aspect, the invention provides a method of analyzing a composition of the current application, the method involving:

performing one or more bootstrapping iterations, each iteration involving selecting one or more responses from each of the capture agent amounts; fitting the selected responses to a curve; and calculating a y-intercept for a linear portion of the curve; and calculating a mean of the y-intercepts. In one embodiment, the iterations further involves removing outliers. In another embodiment, the responses are measured with an imaging device. In another embodiment, the imaging device is a fluorescence imaging device. In another embodiment, the method is a computer-implemented method.

In another aspect, the invention provides a method of generation of an algorithm for analyzing the composition of the current application, the method involving performing one or more bootstrapping iterations, each iteration involving selecting one or more responses from each of the capture agent amounts; fitting the selected responses to a curve; and calculating a y-intercept for a linear portion of the curve.

The invention provides compositions comprising compositions and methods for measuring the abundance of one or more target analytes in a sample. Compositions and articles defined by the invention were isolated or otherwise manufactured in connection with the examples provided below. Other features and advantages of the invention will be apparent from the detailed description, and from the claims.

DEFINITIONS

By "agent" is meant any small molecule chemical compound, antibody, nucleic acid molecule, polypeptide, or fragments thereof.

By "analyte" is meant an agent to be detected in a sample. Exemplary analytes include chemical compounds, polynucleotides (e.g., circulating DNA and RNA) and fragments thereof, polypeptides and fragments thereof, and cells (e.g., circulating cancer cells)

By "capture agent" is meant an agent that specifically binds an analyte of interest in a sample. Exemplary capture agents include antibodies and fragments thereof, aptamers, antigens, synthetic peptides, synthetic polynucleotides, particles, or nanoparticles. In particular embodiments, the capture agent captures the analyte based on physical affinity, charge, magnetic attraction, chemical conjugation, conformation, hybridization, ligand-receptor interaction. In one embodiment, a lectin or antibody, or aptamer is used to capture a cell.

By "alteration" is meant a change (increase or decrease) in the level of an analyte relative to a reference.

By "binding" is meant having a physicochemical affinity for a molecule. Binding is measured by any of the methods of the invention. In one embodiment, binding is detected by detecting hybridization of a detectable nucleic acid probe to a target analyte. In another embodiment, a target analyte bound to a capture agent fixed to a substrate is detected by antibody binding, wherein the antibody comprises a detectable moiety.

By "biological sample" is meant any tissue, cell, fluid, or other material derived from an organism (e.g., human subject, pathogen, plant).

By "marker" is meant a polypeptide or polynucleotide or any biological or non-biological entity that is differentially present in a sample taken from a subject having a disease or disorder relative to a reference. A marker is one type of analyte.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable moiety" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "detection unit" is meant an individual element for analyte detection. The detection unit defines an element of a composition comprising a set of detection units.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

As used herein a "nucleic acid or oligonucleotide probe" is defined as a polynucleotide capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target gene of interest.

By "reference" is meant a standard or control condition.

By "specifically binds" is meant a capture agent that recognizes and binds an analyte of the invention, but which does not substantially recognize and bind other molecules in a sample.

By "subject" is meant a mammal, including, but not limited to, a human or non-human mammal, such as a bovine, equine, canine, ovine, plant, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

The following detailed description, given by way of examples, but not intended to limit the invention to specific embodiments described, may be understood in conjunction with the accompanying drawings, incorporated herein by reference. Various preferred features and embodiments of the present invention will now be described by way of non-limiting examples and with reference to the accompanying drawings in which:

FIG. 1A shows a capturing agent spotted in N concentration levels in a gradient with M replicates. FIG. 1B represent an analog signal from affinity capturing by a capturing agent spotted in N concentration levels in a gradient with M replicates. FIG. 1C represents the digitization of an analog signal from affinity capturing by a capturing agent spotted in N concentration levels in a gradient with M replicates. Proportions of the positive spots (number of positive spots over total number of spots) among replicates are listed for each spotting concentration levels. FIG. 1D shows curve fitting using the sequence of pairs of proportions of positive spots and spotting concentrations {(x(i), b(i)), i=1, 2, . . . , N} and an example of how such a curve can be used to produce quantitative measurement of analyte concentration in the given specimen. FIG. 1E is a graph showing the relation of the horizontal position of fitted curve (or h distance) to concentration of analyte in a given specimen.

FIG. 2A shows the array design without and with corruption of zero-mean Gaussian noise and variability in array printing that corresponds to a CV (coefficient of variation) of 30%, respectively. FIG. 2B compares the simulation results of the array processed using two specimens of different levels of the target analyte. An additional zero-mean Gaussian noise, also corresponding to a CV of 30%, was added during the array processing and scanning procedures. FIG. 2C provides images of arrays after conversion of unit data into binary values. FIG. 2D plots the results of curve-fitting using the two arrays' simulated data. Finally, FIG. 2E are fitted curves using arrays processed with specimens of low (left), mediate (middle), and high (right) analyte concentrations. FIG. 2A represents an affinity capturing array of spotted capturing agent, with N=96 capturing agent concentration levels and M=48 replicate units at each level. Bright blue corresponds to higher spotting concentration level and dark black corresponds to lower spotting concentration level. Left: the ideal array with no variance in array spotting, right: the same array corrupted with a zero-mean normally distributed noise that resulted in a 30% CV (coefficient of variation) in actually spotted concentration levels. FIG. 2B shows simulated analog signals from the noise-corrupted affinity capturing array using the competitive immunoassay model (Campfield, 1983; Chan, 1987) with additional zero-mean normally distributed noise in array processing and signal detection, resulted in an additional analytical variance of 30% CV. Bright green indicates higher analog signal from affinity capturing and dark black indicates lower analog signal. The array on the left is processed with a specimen that has a lower concentration of the target analyte than the specimen processed by the array on the right. FIG. 2C shows the Binary results from digitization of the analog signals of the affinity capturing arrays in FIG. 2B. Red indicates positive signal or 1 and black indicates negative signal or 0. FIG. 2D shows a plot of proportions of positive spots among M=48 replicates at N=98 concentration levels and the fitted curves. The curve f(b) used for this embodiment is a truncated sigmoid function with four parameters A(1), A(2), A(3), and A(4):

Let $y=A(3)/(1+\exp(A(1)*X+A(2)))$, then

If $y>A(4)$, $f(b)=y-A(4)$; else $f(b)=0$.

Figure 2A:
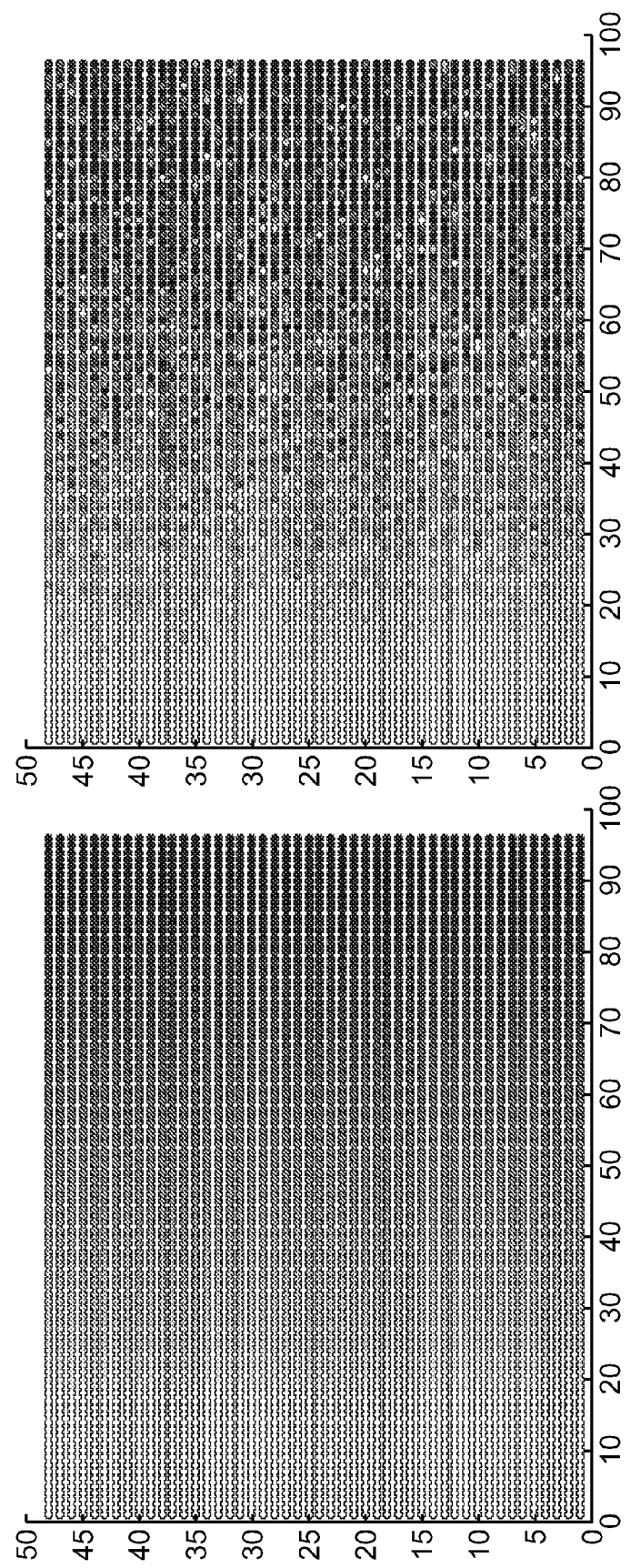
FIGS. 2A-2E provide results of a simulation using a competitive immunoassay model. A column in the image corresponds to replicate units (M=48) of the same capturing agent concentration level while a row in the image represents units (N=96) printed with capturing agent in a discrete gradient. In actual application the capturing units are to be printed with randomized spatial patterns to eliminate analytical variability being confounded with expected signals from units. The figures can be viewed as images of detected signals from units in an actual array rearranged by capturing agent concentration levels.
Figure 2B:
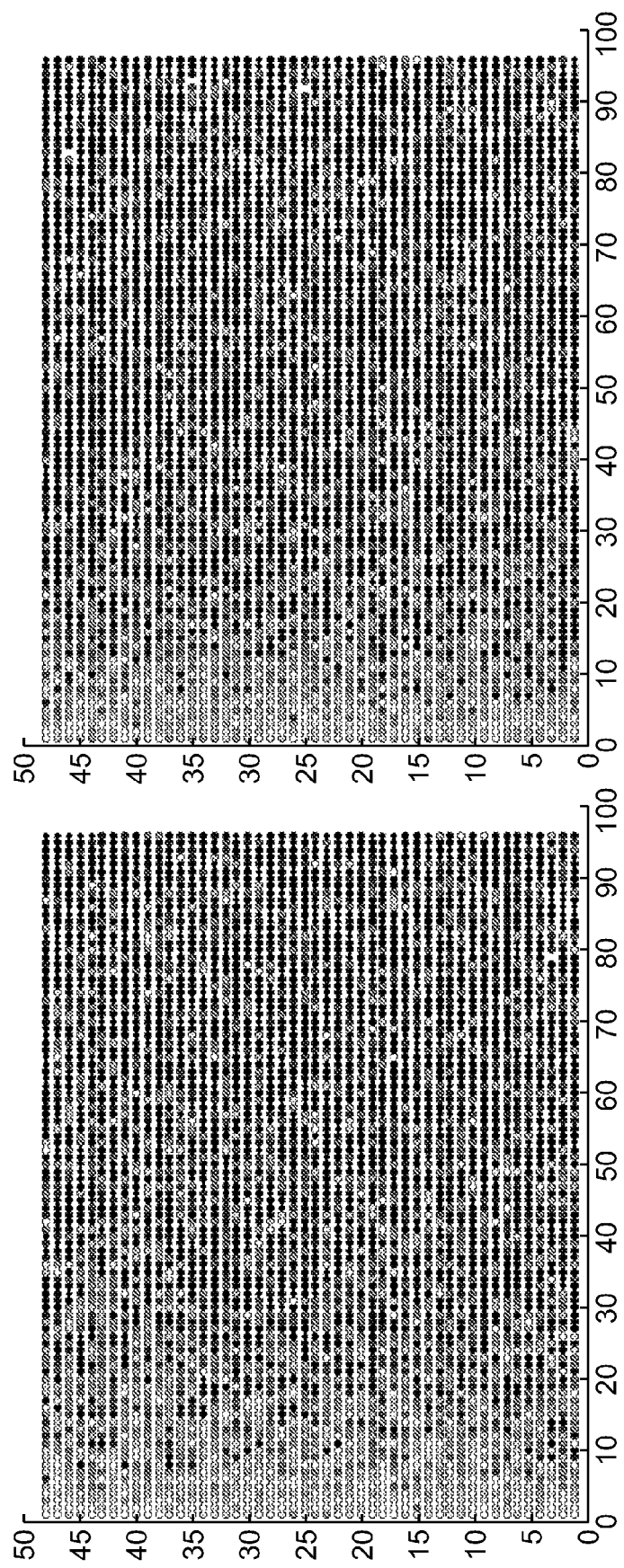
Figure 2C:
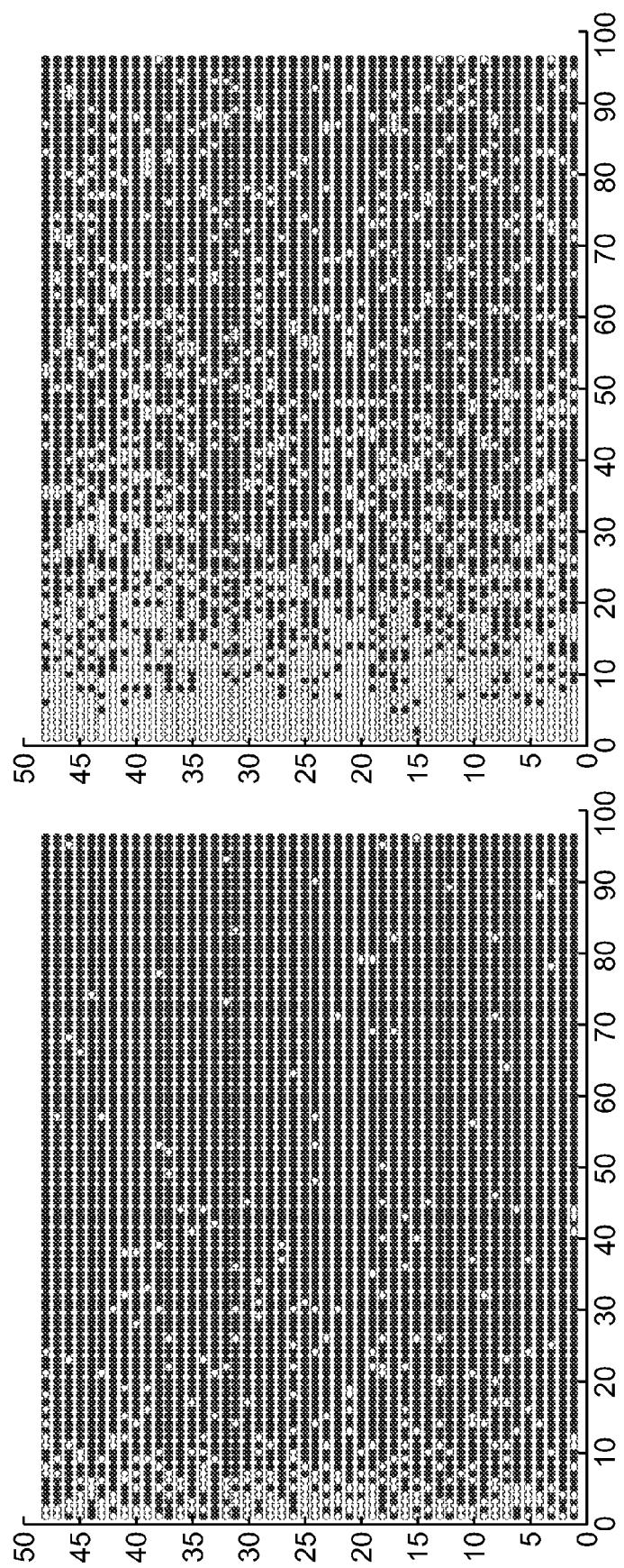
Figure 2D:
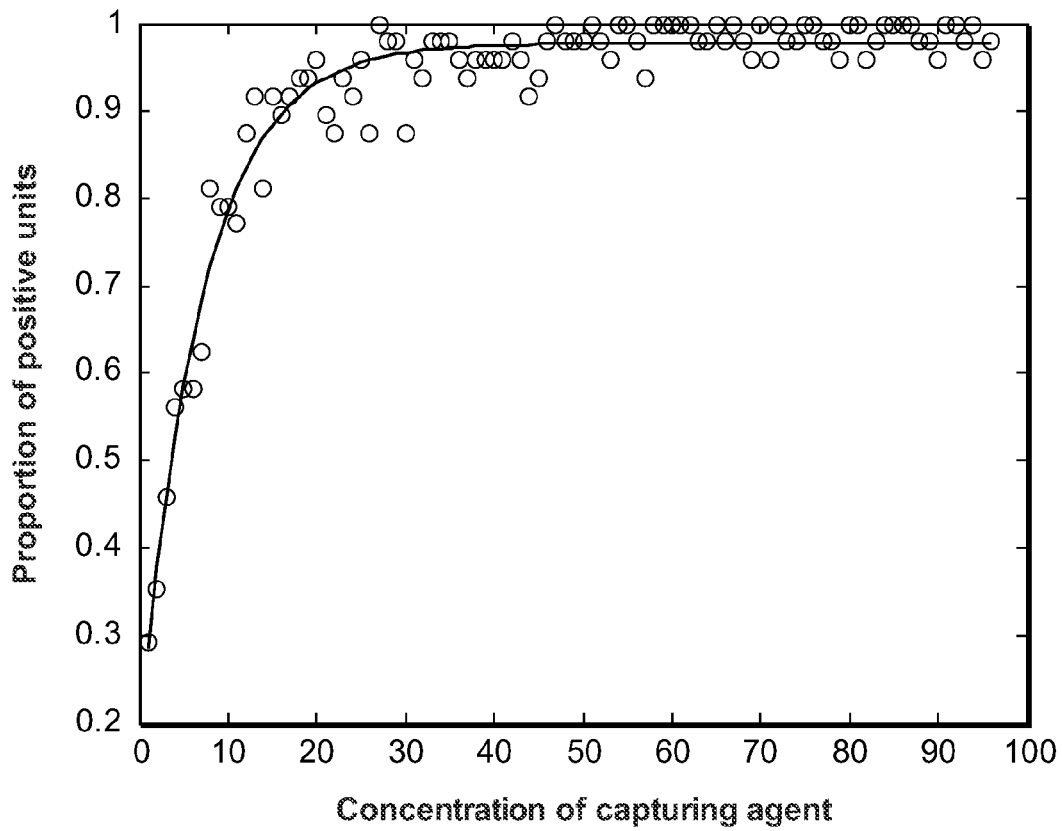
Figure 2D:
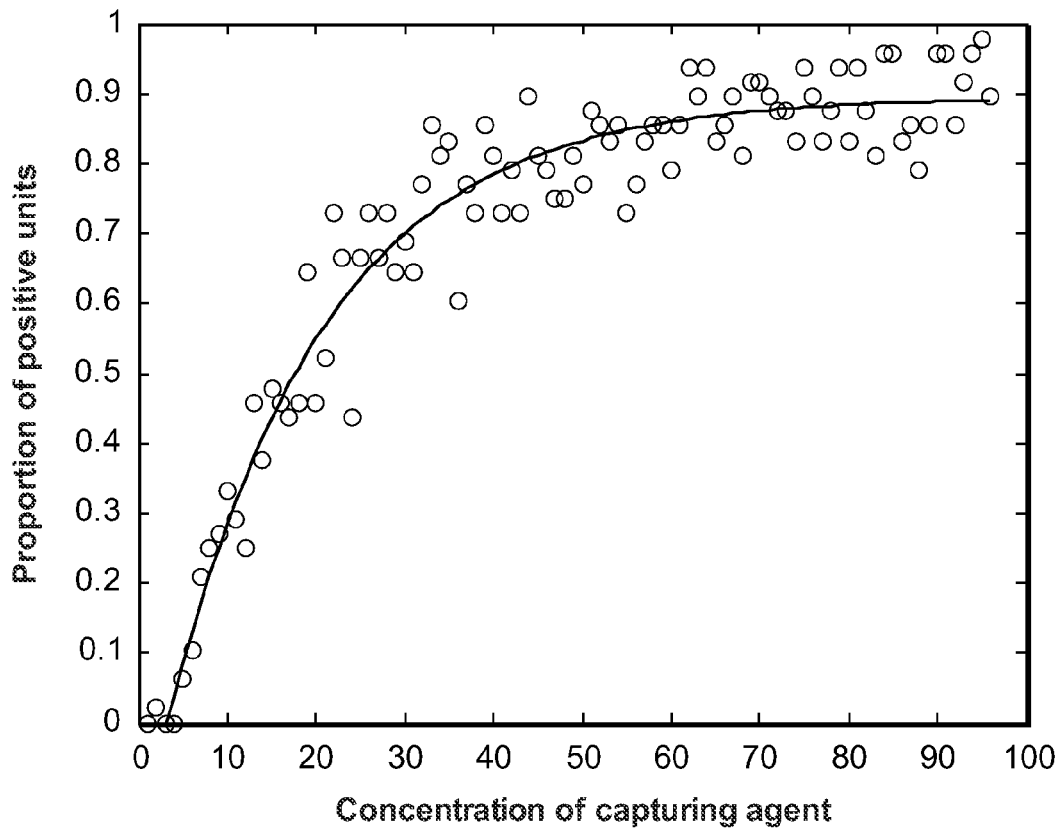
Figure 2E:
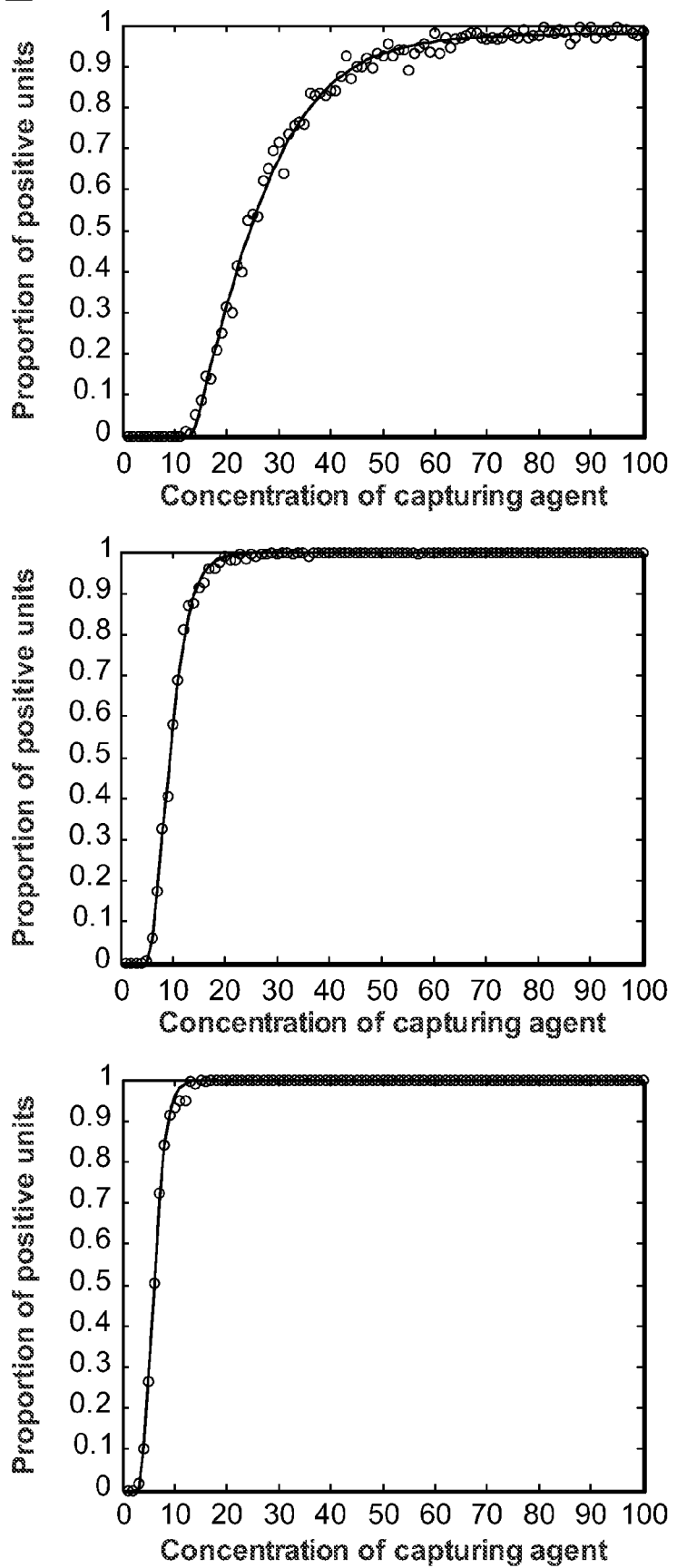

FIG. 2E shows simulated results and fitted curves using the array in FIG. 2A (right side) processed with specimens of low (left), mediate (middle), and high (right) analyte concentrations. Notice the corresponding shift of curves from right towards left.

Figure 3A:
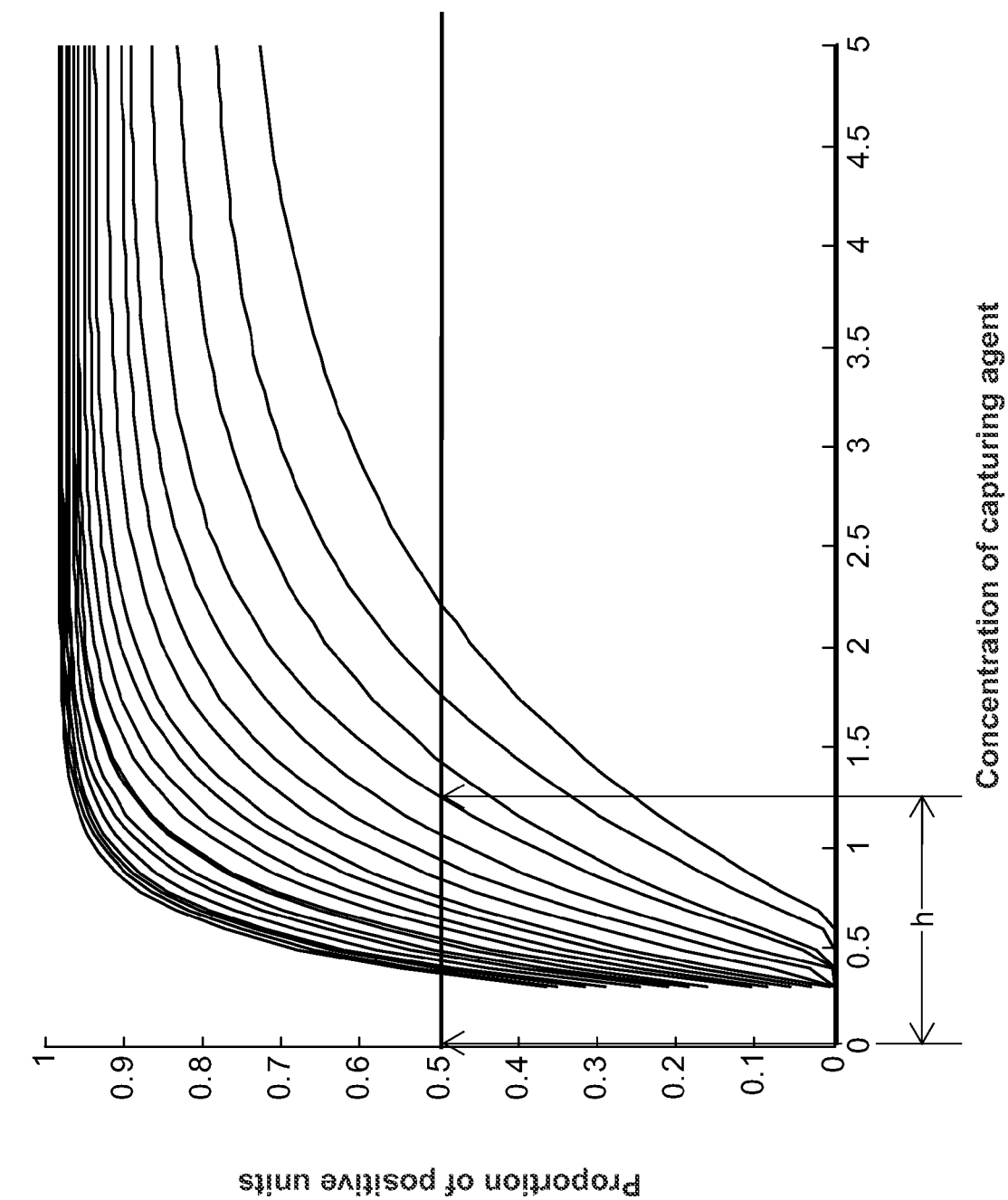
Figure 3B:
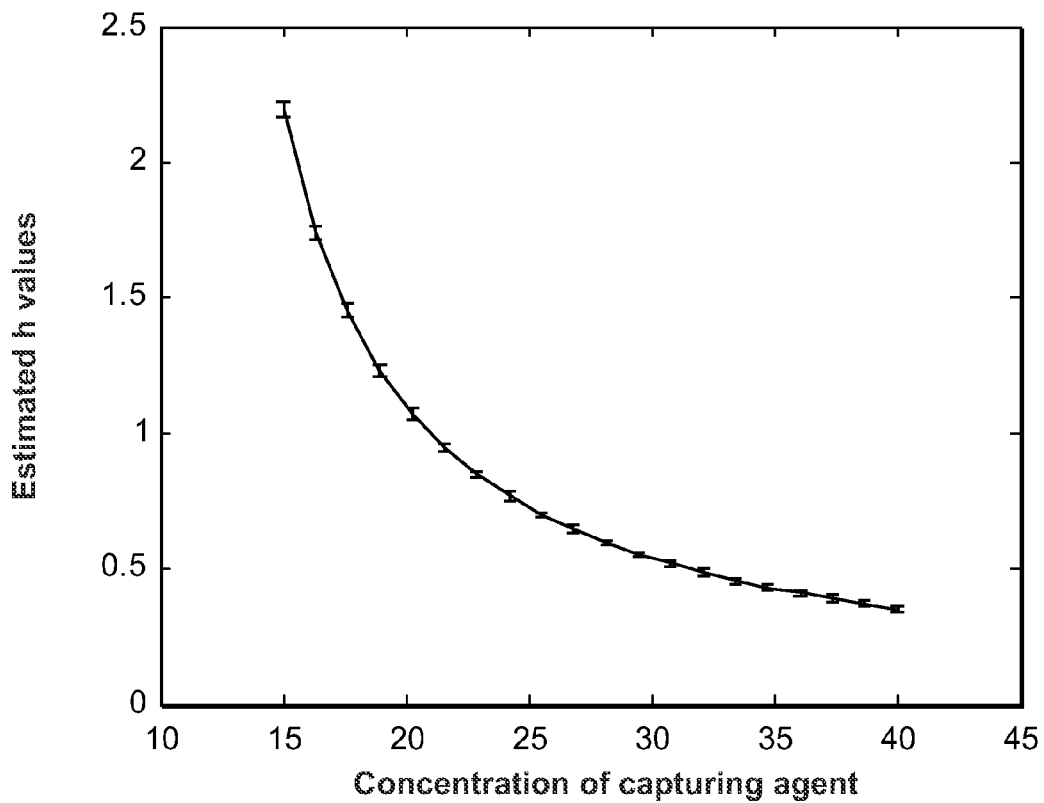
Figure 3C:
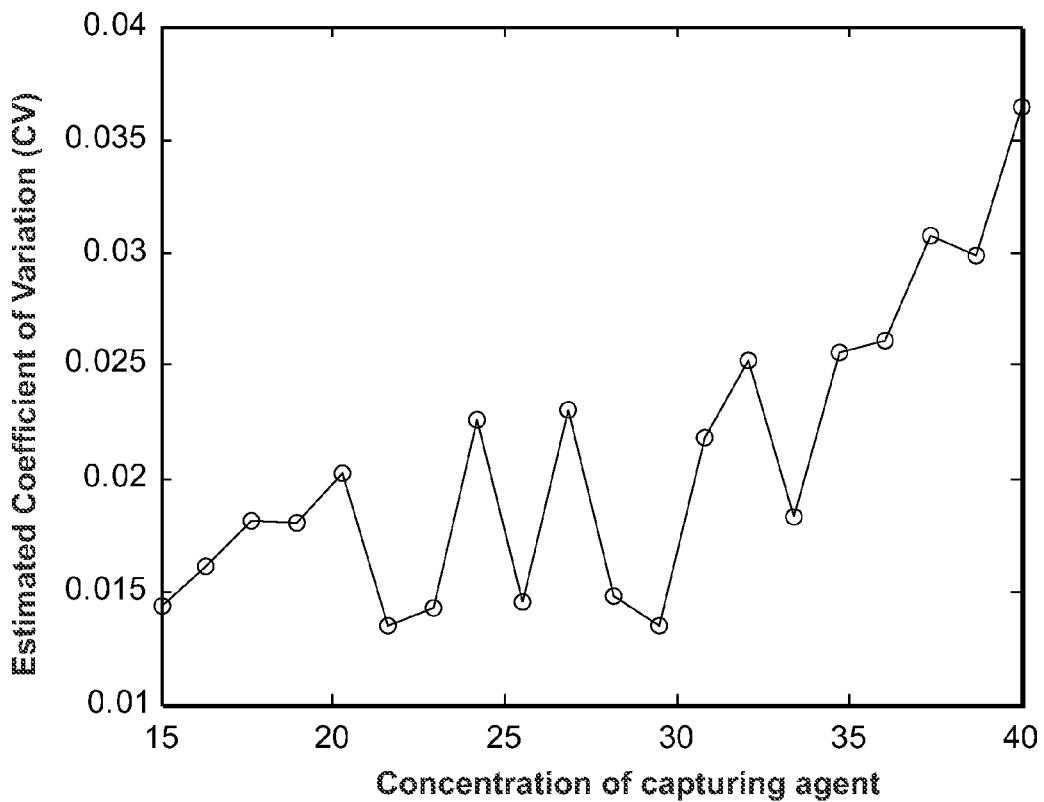
Figure 4:
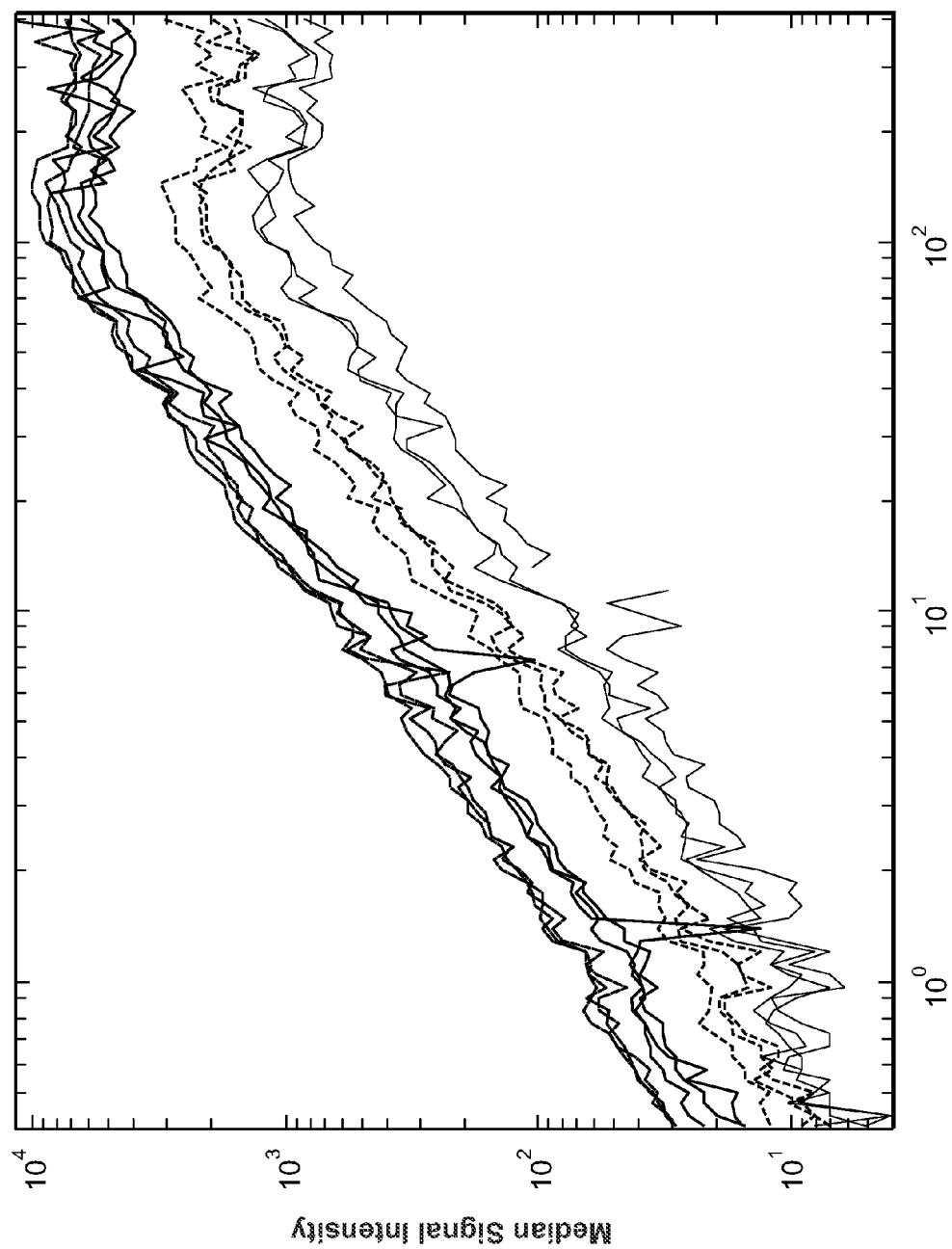

FIG. 3 provides an analysis of results obtained in a simulation by processing the arrays with samples having a target analyte present in varying abundance. The resulted fitted curves are plotted in FIG. 3A, which also demonstrates how the distance h value was measured for each of the curves. In FIG. 3B, the h values of individual curves were plotted against the corresponding known analyte concentrations in the samples, demonstrating a smooth response curve over the entire analyte concentration range. The CVs of h values were estimated by repeating the above simulation procedures 20 times. In FIG. 3C, it can be seen that the maximum CV was <4% even though both the array printing and processing had each been subjected to an added variability of 30% CV. FIG. 3A includes an analysis of simulated results obtained using the array in FIG. 2A (right side) showing fitted curves shifting from left to right, corresponding to processing the array with specimens of increasing analyte concentrations. For each fitted curve, an h value is defined as the horizontal distance of the curve at f(x)=0.5 from the origin. FIG. 3B provides an plot of estimated h values of the array processed by specimens of increasing analyte concentrations. FIG. 3C provides a Bootstrap estimation of analytical variability of h values. Notices that the CVs are <4% even though the individual affinity capturing spot had 30% CV in both capturing agent spotting and array process/signal detection FIG. 4 provides a log-log scale plot of median signal intensities estimated using the M=40 replicate units at the known spotting concentration levels of TRIM21 antigen based on data from arrays processed with pooled human sera at ×200 (red lines), ×400 (blue lines), ×800 (green lines, and ×1600 (magenta lines) dilutions.

Figure 5:
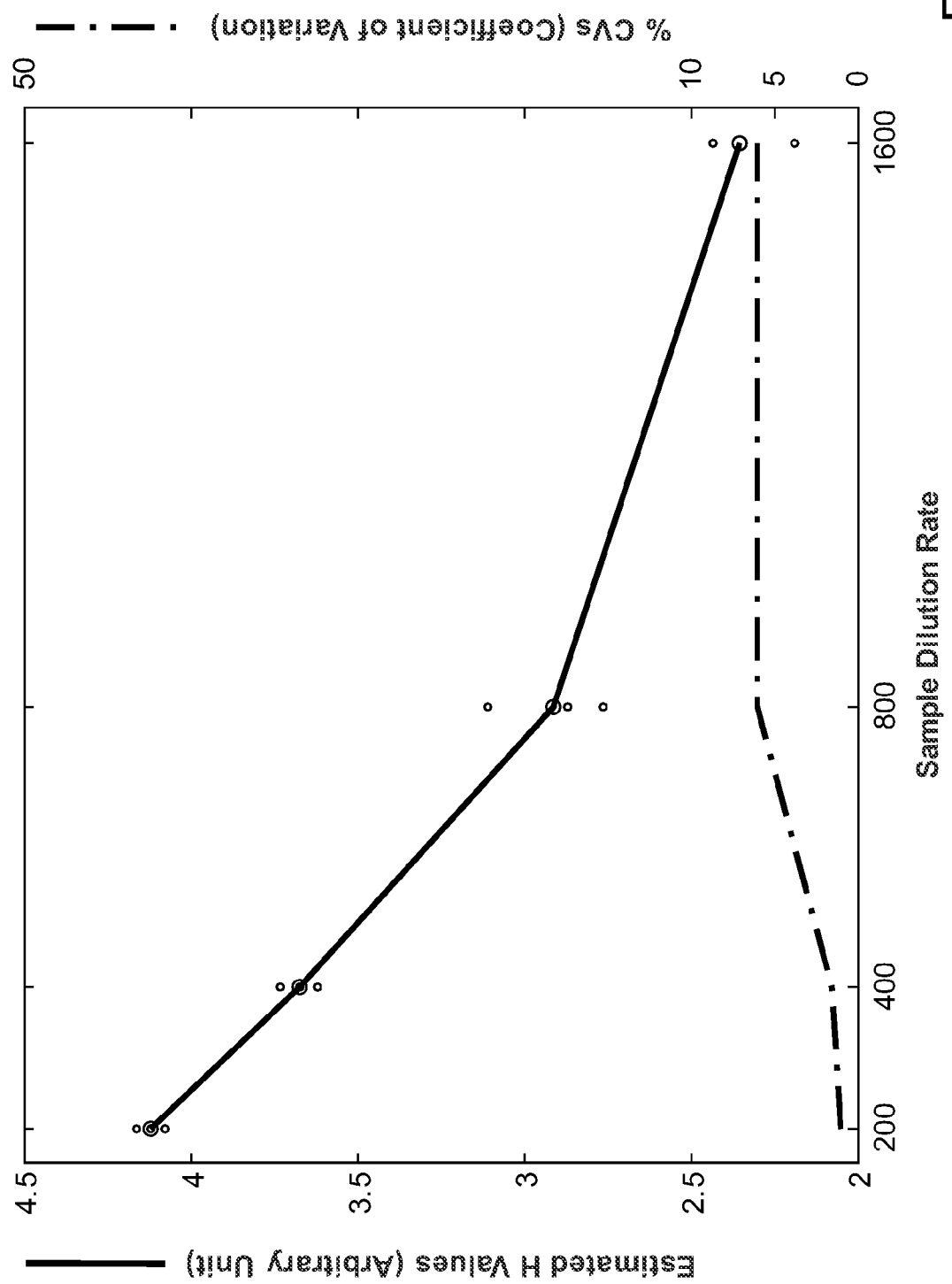

FIG. 5 is a graph showing estimated h values by Algorithm #2 in one experiment plotted against the dilution rate of the pooled patient sera (proportional to the descending abundance of TRIM21 auto-antibodies in samples). The results demonstrate good concentration-dependent responses (solid blue line). FIG. 5 shows results of a first experiment, where overall CVs of 1.0%, 1.6%, 6.0%, and 6.0% (dashed green line) were observed on samples at ×200, ×400, ×800, and ×1600 dilutions, respectively.

Figure 6:
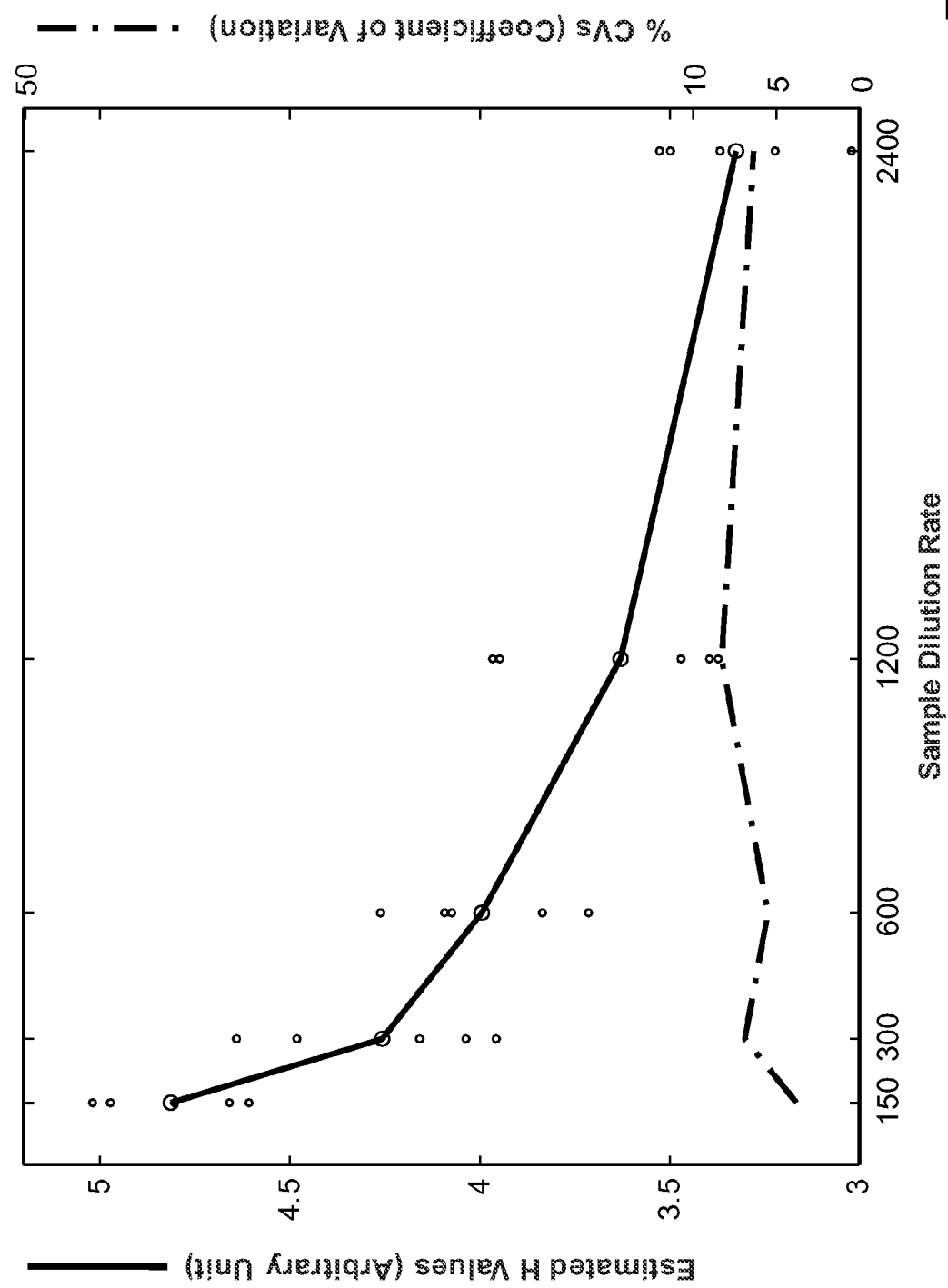

FIG. 6 is a graph showing estimated h values by Algorithm #2 in another experiment plotted against the dilution rate of the pooled patient sera (proportional to the descending abundance of TRIM21 auto-antibodies in samples). The results demonstrate good concentration-dependent responses (solid blue line). FIG. 6 shows results of a first experiment, where overall CVs of 3.8%, 6.9%, 5.5%, 8.3%, and 6.3% (dashed green line) were observed on samples at ×150, ×300, ×600, ×1200, and ×2400 dilutions, respectively.

Figure 7:
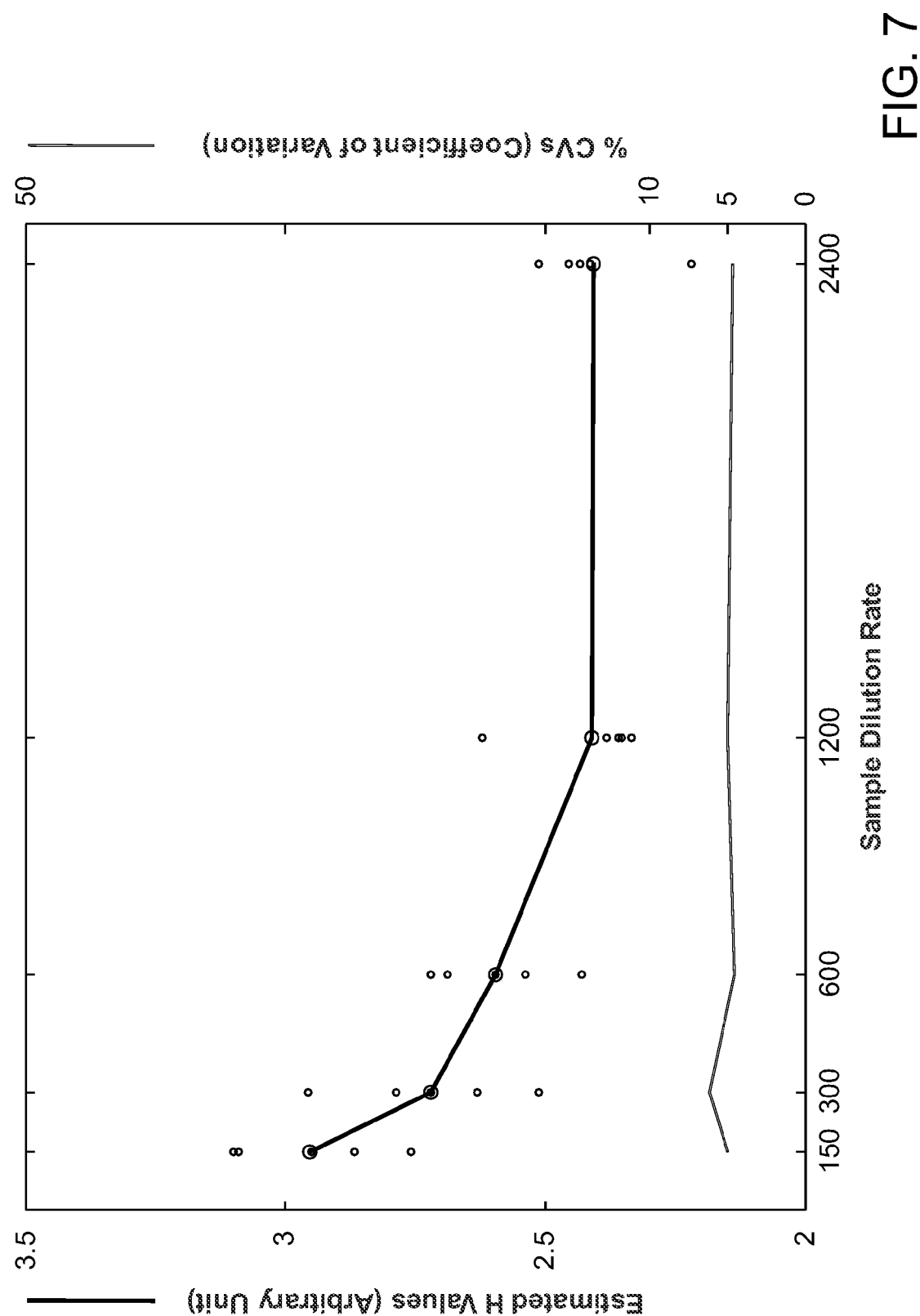

FIG. 7 shows that estimated h values by Algorithm #2 in the same experiment as in FIG. 5 plotted against the dilution rate of the pooled patient sera (proportional to the descending abundance of TRIM21 auto-antibodies in samples). The number of discrete levels in the capturing agent gradient was reduced from 96 to 24. The results still demonstrate good concentration-dependent responses and small CVs. However, the response curve become flat for sample dilutions>×1200.

Figure 8:
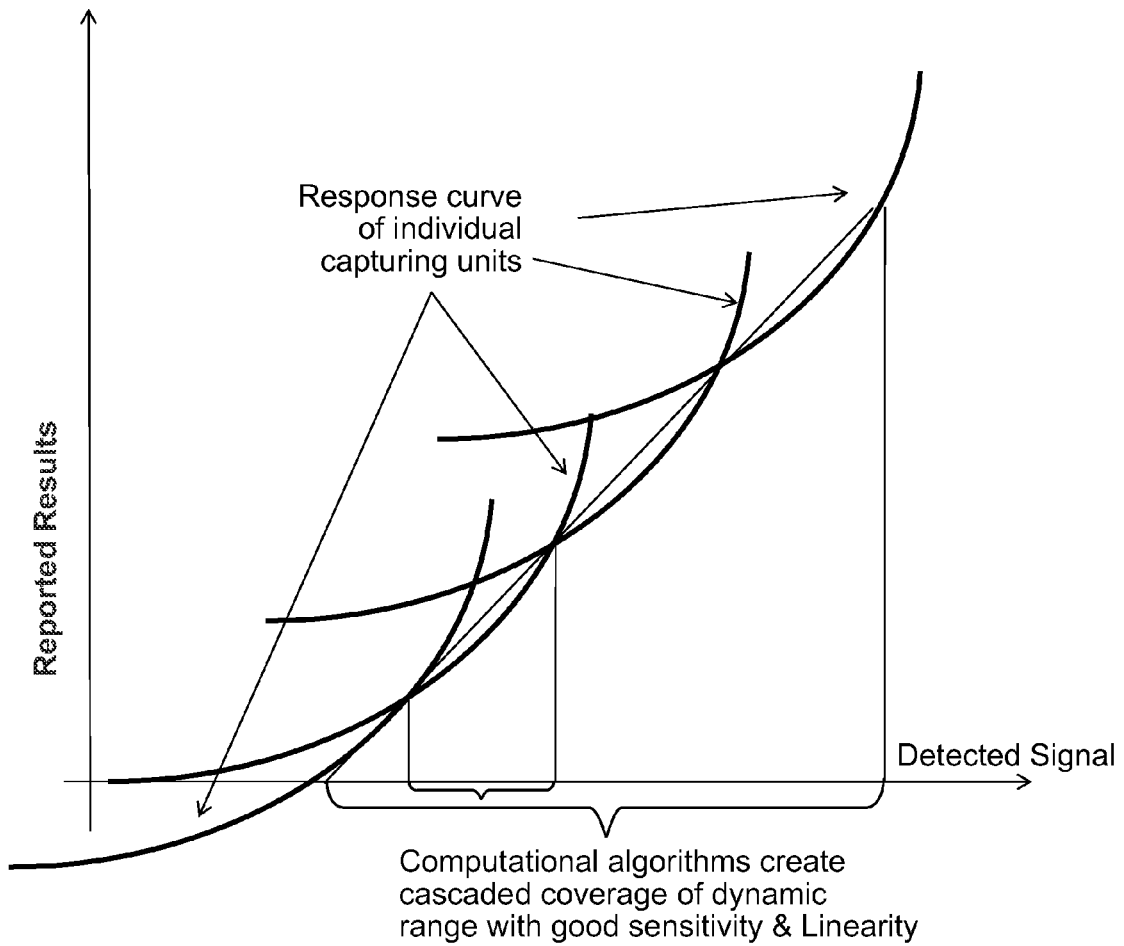

FIG. 8 is a schematic drawing, which illustrates the advantages achieved by overlapping and stacking a large number of small response curves (as represented by the individual capturing units in the new array design). The current invention computationally constructs equivalently a cascaded response curve with a much broader dynamic range.

Figure 9:
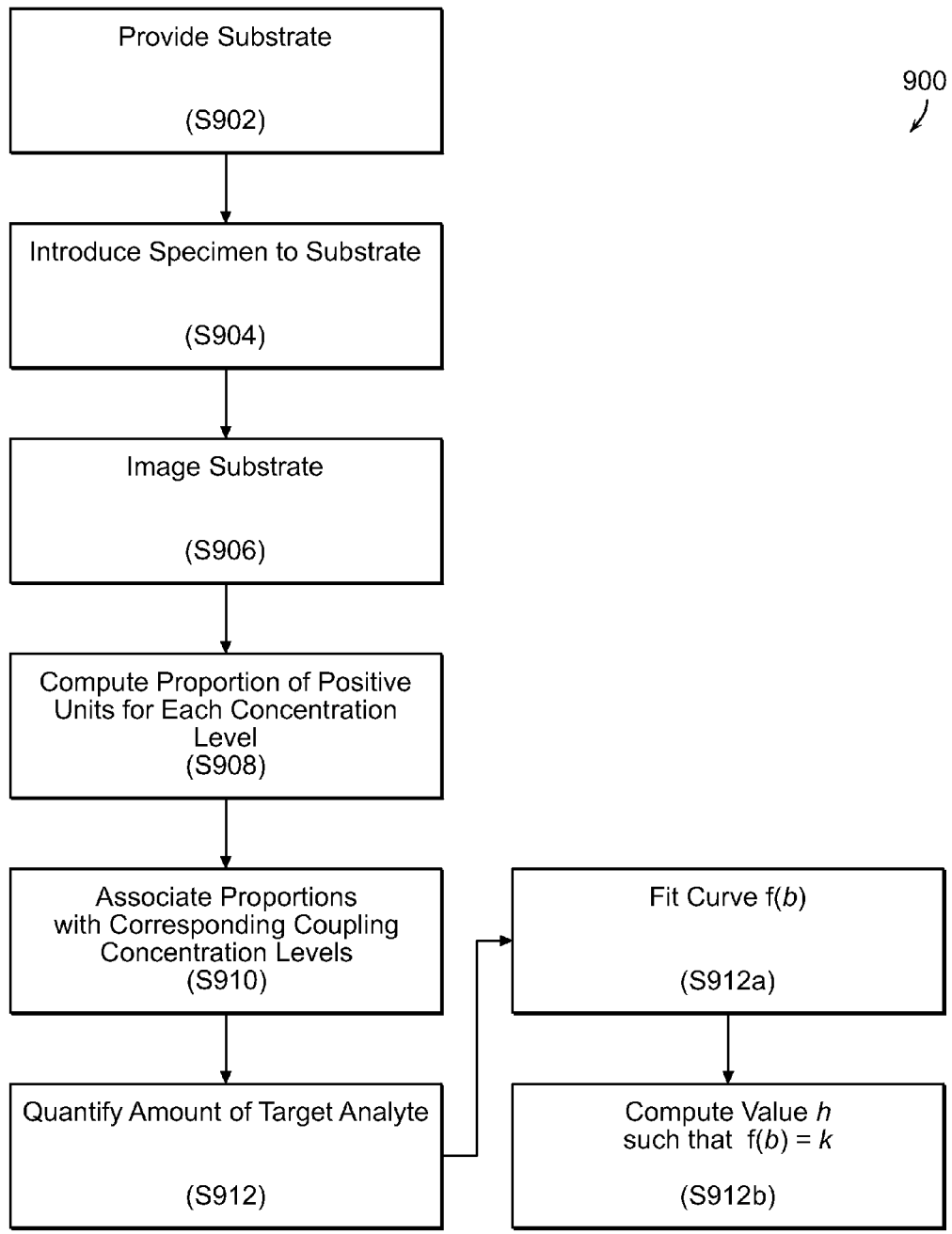
Figure 10:
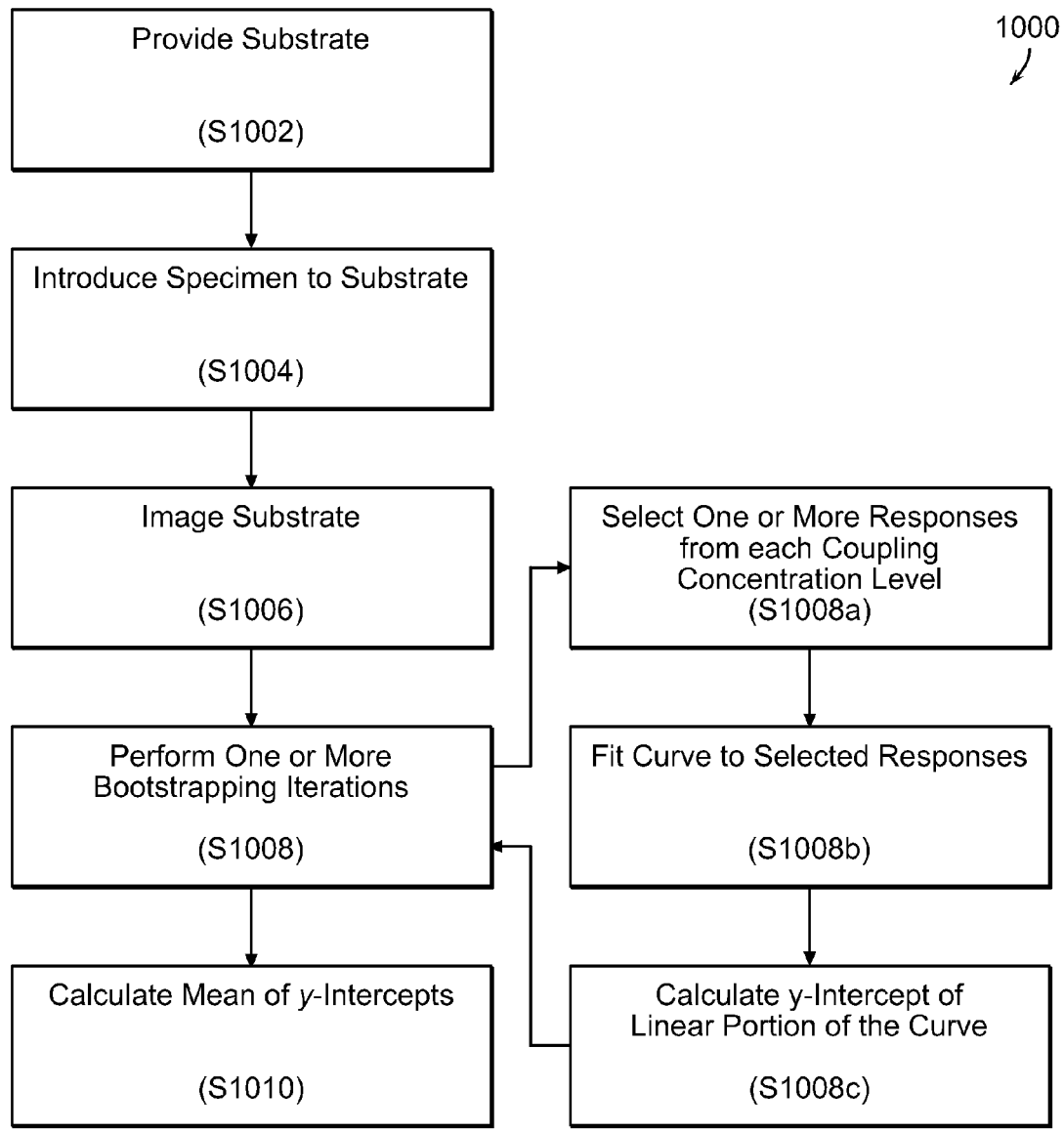

FIGS. 9 and 10 depicts methods of analyzing a composition.

DETAILED DESCRIPTION OF THE INVENTION

The invention features compositions and methods that are useful for precisely determining the amount of one or more analytes present in a sample.

The invention is based, at least in part, on the discovery that the use of a concentration gradient of an affinity-capturing agent that recognizes a target analyte provides the dynamic range of that analyte in the sample, which range can be converted using a computation algorithm to a precise and reproducible readout of the amount of analyte in said sample. This provides for increased precision and reproducibility relative to the use of a single concentration of the affinity-capturing agent. The invention further provides computational algorithms that take advantage of the aforementioned composition design to computationally stack and overlap multiple response curves of individual capturing units to achieve equivalent response curves with a much larger dynamic range; and to aggregate information from replicates of units coupled with varying capturing agent concentrations to achieve analytical performance that is much better than what can be achieved using replicates alone.

Compositions for Analyte Detection

The invention provides compositions, devices, and systems for the detection of an analyte in a test sample. In one embodiment, the invention provides a composition (e.g., microarray, protein chip, polynucleotide chip, collection of beads, microscope slide, a microfluidic plate, a 96-well plate, or other suitable format) for measuring the abundance of one or more target analytes in a sample that contains a set of detection units (e.g., capture reagent spot, single bead, single well). Each detection unit contains a discrete amount of a capture agent (e.g., small compound, such as biotin, polypeptide, such as an antibody or fragment thereof, antigen, peptide, polynucleotide, such as RNA, DNA, an aptamer) fixed to a substrate. The amount of capture agent varies within the set of detection units, such that the amount of capture reagent present in the set forms a concentration gradient.

In one embodiment, a single detection unit in the set contains a given amount of capture agent that differs from the amount of capture agent present in any other detection unit in the set. The variation between detection units in a set may be linear or may vary exponentially over the set to form a concentration gradient. If desired, the amount of capture agent present may be duplicated in two or more detection units. Detection units having the same amount of capture agent are said to be replicates. Nevertheless, the amount of capture agent differs between detection unit replicates present in the set, such that the detection units present in the set form a concentration gradient. The number of detection units within the set is optimized to reduce analytical variability or to expand the dynamic range of the assay.

In another embodiment, the invention provides a test device comprising one or more compositions of the invention. Exemplary test devices include columns comprising a collection of beads, a sheet comprising one or more microarrays, a plate comprising one or more microarrays or microfluidic arrays, a two-dimensional (2D) or 3-dimensional (3D) structure comprising one or more collections of 2D surfaces or 3D shapes.

The invention provides for the design of single or multiplexed assays for the detection and quantitative measurement of one or a plurality of analytes in a specimen. Desirably, the compositions of the invention have the following features: 1) take advantage of the noise-resistance ability of digitized signal detected from affinity capture, 2) take advantage of the capacity of high-density arrays to improve the analytical performance of an assay by increasing the assay's precision, reproducibility, and/or specificity; and 3) aggregating results from affinity capturing by capture agents spotted in a gradient to expand the dynamic range of multiplexed tests, and lessen the difficulties in mixing multiple tests in a single assay.

In particular embodiments, the invention provides methods for designing a "digitized" assay. The methods involve spotting a capture agent on an array or otherwise fixing a capture agent to a substrate. Preferably, the capture agent is fixed to the substrate in multiple (N) concentration levels along a gradient. If desired, multiple (M) replicates of the capture agent are present at each of the concentration level. The number of concentration gradient levels N is optionally chosen such that it provides a sufficient quantification resolution in measurement required by the application.

In the course of the assay, a composition of the invention is contacted with a sample, such that an analyte present in the sample binds to the capture agent and is retained on the substrate. Binding of the analyte to the capture agent is subsequently detected using any method known in the art. In one embodiment, binding is detected by contacting the substrate with a detectable reporter that binds to the analyte or to the analyte/capture agent pair. A detectable signal indicative of analyte/capture agent binding is detected by a "reader" (e.g., a device, such as a mass spectrometer, plate reader, scintillation counter) that detects, for example, luminescence, color, turbidity, radioactivity, or any other detectable signal.

The lower and upper bounds of the concentration gradient levels are optionally chosen such that the resulting signal (i.e., affinity capture signal) sufficiently covers the dynamic range of the corresponding target analyte in the specimen as required by the application. The number of replicates M at each concentration level is also optionally chosen such that a desired level of quantification precision (confidence interval) in measurement is reached through statistically-principled calculations. Optionally, the replicates are spotted on the array in a randomized pattern to reduce the effect of uneven analytical variability in assay processing. Still optionally, the replicates can also be spotted on the array in a pattern designed to facilitate the numerical analysis of the results.

If desired, the compositions of the invention are adapted to allow multiple tests to be conducted on the same compositions to create a multiplexed assay. In certain embodiments, the lower and upper bounds of the concentration gradient levels are chosen such that they cover the entire expected dynamic ranges of the targets in the specimens plus a sufficiently large margin at both lower and upper ends.

The signal from each detection unit (e.g., bead, spot) is reported as a digitized value, typically as either positive (1) or negative (0) based on certain criteria, typically a threshold of the detected signal. The proportion of positive spots $x(i)=m(i)/M$, where $m(i)$ is the number of spots reported positive at concentration level i, and $i=1, 2, \ldots, N$, is computed for each of the N spotting concentration levels of the capturing agent. An optional procedure may be used to remove outliers in computing the proportion of positive spots. The sequence of pairs $\{(x(i), b(i)), i=1, 2, \ldots, N\}$ is then used to quantify the concentration of target analyte in the sample.

In various embodiments, the sequence of pairs of proportions of positive spots and spotting concentration levels $\{(x(i), b(i)), i=1, 2, \ldots, N\}$ in the above described method is used to fit a parameterized curve f(b). The resulting parameters of the curve are then used to quantify the concentration of target analytes in the sample. In other embodiments, the parameters of the fitted curve are used to compute a value h defined as the horizontal distance between f(h)=0.5 and the origin and use it as a quantitative measure of analyte concentration in specimen.

In other embodiments, the spacing between adjacent concentration levels in spotting capture agents is optionally adjusted in order to use a specific shape of curves to fit the sequence of pairs of proportions of positive spots $\{(x(i), b(i)), i=1, 2, \ldots, N\}$ in the above described method or to obtain a desired resolution in quantitative measurement of the analytes.

In still other embodiments, the choice of range and/or resolution of the concentration gradient for a particular capturing agent can be determined experimentally and computationally to match the expected dynamic range of a target analyte in specimens. The method comprises 1) during assay development, spotting the capturing agent in very fine resolution and in an overly wide range with a large number of replicates; 2) contacting the composition of the invention with a set of samples with varying and known concentration levels of a target analyte(s) covering the entire expected dynamic range of the analyte in the sample; and 3) computationally searching for an optimal range and/or resolution of spotting concentration levels for the capture agent using predefined criteria.

In other embodiments, the optimal range and/or resolution of spotting concentration levels for the capturing agent comprises: 1) for each spotting range/resolution being evaluated, computing the h value, defined as the horizontal distance between f(h)=0.5 and the origin (FIG. 3A), and the variance of h by statistical methods such as bootstrap, for each of the specimens with different known concentrations of the target analyte; 2) creating a curve of h values against the corresponding known analyte concentrations in a gradient; 3) evaluating the analytical performance of the current spotting range/resolution of capturing agent and use the results as the basis for selection of a spotting range/resolution of capturing agent for the actual assay.

In other aspects, the evaluation of analytical performance of a particular spotting range/resolution of capturing agent is based on maximizing the local slope of the h vs. known analyte concentration, and/or minimizing analytical variances, while at the same time minimizing the number of spotting concentration levels and/or the number of replicates at each spotting concentration level.

As described herein, compositions of the invention include sets of hybridizable detection units present in a microarray. Polypeptides and polynucleotides, and fragments thereof, useful in arrays of the invention may be organized in an ordered fashion such that each element is present at a specified location (i.e., an addressable location) on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

To produce a composition comprising hybridizable polynucleotides, oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

In certain embodiments, a nucleic acid molecule (e.g. RNA or DNA) may be used to produce a hybridization probe. In one embodiment, a biological sample is derived from a subject, preferably as a tissue sample (e.g. a tissue sample obtained by biopsy) or a bodily fluid sample (such as blood, cerebrospinal fluid, phlegm, saliva, or urine). For some applications, cultured cells or other tissue preparations may be used. The mRNA is isolated according to standard methods, and cDNA is produced and used as a template to make complementary RNA suitable for hybridization. In one embodiment, the RNA is amplified in the presence of fluorescent nucleotides, and the labeled probes are then incubated with a microarray or other composition of the invention to allow the probe sequence to hybridize to complementary oligonucleotides fixed to the microarray.

Incubation conditions are adjusted such that hybridization occurs with precise complementary matches or with various degrees of less complementarity depending on the degree of stringency employed. For example, salt concentration, organic solvent percentage, and temperature conditions are varied to achieve the desired stringency. Varying additional parameters, such as hybridization time, the concentration of detergent, e.g., sodium dodecyl sulfate (SDS), and the inclusion or exclusion of carrier DNA, are well known to those skilled in the art. Useful variations will be readily apparent to those skilled in the art. A detection system may be used to measure the absence, presence, and amount of hybridization for all of the distinct sequences simultaneously (e.g., Heller et al., Proc. Natl. Acad. Sci. 94:2150-2155, 1997). Preferably, a scanner is used to determine the levels and patterns of fluorescence.

Polypeptides and fragments thereof may be analyzed using compositions of the invention, Typically, such compositions feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins are spotted on a substrate using any convenient method known to the skilled artisan (e.g., by hand or by inkjet printer). Preferably, such methods retain the biological activity or function of the protein bound to the substrate (Ge et al., supra; Zhu et al., supra).

A composition of the invention is hybridized with a detectable probe. Such probes can be polypeptide, nucleic acid, or small molecules. Probes can also include antibodies, candidate peptides, nucleic acids, or small molecule compounds derived from a peptide, nucleic acid molecule, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

DETAILED DESCRIPTION OF THE INVENTION

The invention features compositions and methods that are useful for precisely determining the amount of one or more analytes present in a sample.

The invention is based, at least in part, on the discovery that the use of a concentration gradient of an affinity-capturing agent that recognizes a target analyte improves the dynamic range of detecting the abundance of that analyte in the sample, which can be converted using a computation algorithm to a precise and reproducible readout of the amount of analyte in said sample. This provides for increased precision and reproducibility relative to the use of a single concentration of the affinity-capturing agent. The invention further provides methods of deriving computational algorithms that take advantage of the afore-mentioned composition design to computationally stack and overlap multiple response curves of individual capturing units to achieve equivalent response curves with a much larger dynamic range; and to aggregate information from replicates of units coupled with varying capturing agent concentrations to achieve analytical performance that is much better than what can be achieved using replicates alone.

Compositions for Analyte Detection

The invention provides compositions, devices, and systems for the detection of an analyte in a test sample. In one embodiment, the invention provides a composition (e.g., microarray, protein chip, polynucleotide chip, collection of beads, microscope slide, a microfluidic plate, a 96-well plate, or other 2D or 3D surface or shape of suitable format) for measuring the abundance of one or more target analytes in a sample that contains a set of detection units (e.g., capture reagent spot, single bead, single well). Each detection unit contains a discrete amount of a capture agent (e.g., small compound, such as biotin, polypeptide, such as an antibody or fragment thereof, antigen, peptide, polynucleotide, such as RNA, DNA, an aptamer) fixed to a substrate. The amount of capture agent varies within the set of detection units, such that the amount of capture reagent present in the set forms a concentration gradient.

In one embodiment, a single detection unit in the set contains a given amount of capture agent that differs from the amount of capture agent present in any other detection unit in the set. The variation between detection units in a set may be linear, vary exponentially, or may vary in other nonlinear fashion over the set to form a concentration gradient. If desired, the amount of capture agent present may be duplicated in two or more detection units. Detection units having the same amount of capture agent are said to be replicates. Nevertheless, the amount of capture agent differs between detection unit replicates present in the set, such that the detection units present in the set form a concentration gradient. The number of detection units within the set is optimized to reduce analytical variability or to expand the dynamic range of the assay.

In another embodiment, the invention provides a test device comprising one or more compositions of the invention. Exemplary test devices include columns comprising a collection of beads, a sheet comprising one or more microarrays, a plate comprising one or more microarrays or microfluidic arrays, a two-dimensional (2D) or 3-dimensional (3D) structure comprising one or more collections of 2D surfaces or 3D shapes that can be used to support the immobilization of a capture agent and/or can otherwise facilitate contact between the capture agent and the target analyte.

The invention provides for the design of single or multiplexed assays for the detection and quantitative measurement of one or a plurality of analytes in a specimen. Desirably, the compositions of the invention have the following features: 1) take advantage of the noise-resistance ability of digitized signal detected from affinity capture, 2) take advantage of the capacity of high-density arrays to improve the analytical performance of an assay by increasing the assay's precision, reproducibility, and/or specificity; and 3) aggregating results from affinity capturing by capture agents spotted in a gradient to expand the dynamic range of multiplexed tests, and lessen the difficulties in mixing multiple tests in a single assay.

In particular embodiments, the invention provides methods for designing a "digitized" assay. The methods involve spotting a capture agent on an array or otherwise fixing a capture agent to a substrate. Preferably, the capture agent is fixed to the substrate in multiple (N) concentration levels along a gradient. If desired, multiple (M) replicates of the capture agent are present at each of the concentration level. The number of concentration gradient levels N is optionally chosen such that it provides a sufficient quantification resolution in measurement required by the application.

In the course of the assay, a composition of the invention is contacted with a sample, such that an analyte present in the sample binds to the capture agent and is retained on the substrate. Binding of the analyte to the capture agent is subsequently detected using any method known in the art. In one embodiment, binding is detected by contacting the substrate with a detectable reporter that binds to the analyte or to the analyte/capture agent pair. A detectable signal indicative of analyte/capture agent binding is detected by a "reader" (e.g, a device, such as a mass spectrometer, plate reader, scintillation counter) that detects, for example, luminescence, color, turbidity, radioactivity, or any other detectable signal.

The lower and upper bounds of the concentration gradient levels are optionally chosen such that the resulting signal (i.e., affinity capture signal) sufficiently covers the dynamic range of the corresponding target analyte in the specimen as required by the application. The number of replicates M at each concentration level is also optionally chosen such that a desired level of quantification precision (confidence interval) in measurement is reached through statistically-principled calculations. Optionally, the replicates are spotted on the array in a randomized pattern to reduce the effect of uneven analytical variability in assay processing. Still optionally, the replicates can also be spotted on the array in a pattern designed to facilitate the numerical analysis of the results.

If desired, the compositions of the invention are adapted to allow multiple tests to be conducted on the same compositions to create a multiplexed assay. In certain embodiments, the lower and upper bounds of the concentration gradient levels are chosen such that they cover the entire expected dynamic ranges of the targets in the specimens plus a sufficiently large margin at both lower and upper ends.

The signal from each detection unit (e.g., bead, spot) is reported as a digitized value, typically as either positive (1) or negative (0) based on certain criteria, typically a threshold of the detected signal. The proportion of positive spots $x(i)=m(i)/M$, where $m(i)$ is the number of spots reported positive at concentration level i, and $i=1, 2, \ldots, N$, is computed for each of the N spotting concentration levels of the capturing agent. An optional procedure may be used to remove outliers in computing the proportion of positive spots. The sequence of pairs $\{(x(i), b(i)), i=1, 2, \ldots, N\}$ is then used to quantify the concentration of target analyte in the sample.

In various embodiments, the sequence of pairs of proportions of positive spots and spotting concentration levels $\{(x(i), b(i)), i=1, 2, \ldots, N\}$ in the above described method is used to fit a parameterized curve $f(b)$. The resulting parameters of the curve are then used to quantify the concentration of target analytes in the sample. In other embodiments, the parameters of the fitted curve are used to compute a value h defined as the horizontal distance between $f(h)=0.5$ and the origin and use it as a quantitative measure of analyte concentration in specimen.

In other embodiments, the spacing between adjacent concentration levels in spotting capture agents is optionally adjusted in order to use a specific shape of curves to fit the sequence of pairs of proportions of positive spots $\{(x(i), b(i)), i=1, 2, \ldots, N\}$ in the above described method or to obtain a desired resolution in quantitative measurement of the analytes.

In still other embodiments, the choice of range and/or resolution of the concentration gradient for a particular capturing agent can be determined experimentally and computationally to match the expected dynamic range of a target analyte in specimens. The method comprises 1) during assay development, spotting the capturing agent in very fine resolution and in an overly wide range with a large number of replicates; 2) contacting the composition of the invention with a set of samples with varying and known concentration levels of a target analyte(s) covering the entire expected dynamic range of the analyte in the sample; and 3) computationally searching for an optimal range and/or resolution of spotting concentration levels for the capture agent using predefined criteria.

In other embodiments, the optimal range and/or resolution of spotting concentration levels for the capturing agent comprises: 1) for each spotting range/resolution being evaluated, computing the h value, defined as the horizontal distance between $f(h)=0.5$ and the origin (FIG. 3A), and the variance of h by statistical methods such as bootstrap, for each of the specimens with different known concentrations of the target analyte; 2) creating a curve of h values against the corresponding known analyte concentrations in a gradient; 3) evaluating the analytical performance of the current spotting range/resolution of capturing agent and use the results as the basis for selection of a spotting range/resolution of capturing agent for the actual assay.

In other aspects, the evaluation of analytical performance of a particular spotting range/resolution of capturing agent is based on maximizing the local slope of the h vs. known analyte concentration, and/or minimizing analytical variances, while at the same time minimizing the number of spotting concentration levels and/or the number of replicates at each spotting concentration level.

As described herein, compositions of the invention include sets of hybridizable detection units present in a microarray. Polypeptides and polynucleotides, and fragments thereof, useful in arrays of the invention may be organized in an ordered fashion such that each element is present at a specified location (i.e., an addressable location) on the substrate. Useful substrate materials include membranes, composed of paper, nylon or other materials, filters, chips, glass slides, and other solid supports. The ordered arrangement of the array elements allows hybridization patterns and intensities to be interpreted as expression levels of particular genes or proteins. Methods for making nucleic acid microarrays are known to the skilled artisan and are described, for example, in U.S. Pat. No. 5,837,832, Lockhart, et al. (Nat. Biotech. 14:1675-1680, 1996), and Schena, et al. (Proc. Natl. Acad. Sci. 93:10614-10619, 1996), herein incorporated by reference. Methods for making polypeptide microarrays are described, for example, by Ge (Nucleic Acids Res. 28: e3. i-e3. vii, 2000), MacBeath et al., (Science 289:1760-1763, 2000), Zhu et al. (Nature Genet. 26:283-289), and in U.S. Pat. No. 6,436,665, hereby incorporated by reference.

To produce a composition comprising hybridizable polynucleotides, oligonucleotides may be synthesized or bound to the surface of a substrate using a chemical coupling procedure and an ink jet application apparatus, as described in PCT application WO95/251116 (Baldeschweiler et al.), incorporated herein by reference. Alternatively, a gridded array may be used to arrange and link cDNA fragments or oligonucleotides to the surface of a substrate using a vacuum system, thermal, UV, mechanical or chemical bonding procedure.

In certain embodiments, a nucleic acid molecule (e.g. RNA or DNA) may be used to produce a hybridization probe. In one embodiment, a biological sample is derived from a subject, preferably as a tissue sample (e.g. a tissue sample obtained by biopsy) or a bodily fluid sample (such as blood, cerebrospinal fluid, phlegm, saliva, or urine). For some applications, cultured cells or other tissue preparations may be used. The mRNA is isolated according to standard methods, and cDNA is produced and used as a template to make complementary RNA suitable for hybridization. In one embodiment, the RNA is amplified in the presence of fluorescent nucleotides, and the labeled probes are then incubated with a microarray or other composition of the invention to allow the probe sequence to hybridize to complementary oligonucleotides fixed to the microarray.

Incubation conditions are adjusted such that hybridization occurs with precise complementary matches or with various degrees of less complementarity depending on the degree of stringency employed. For example, salt concentration, organic solvent percentage, and temperature conditions are varied to achieve the desired stringency. Varying additional parameters, such as hybridization time, the concentration of detergent, e.g., sodium dodecyl sulfate (SDS), and the inclusion or exclusion of carrier DNA, are well known to those skilled in the art. Useful variations will be readily apparent to those skilled in the art. A detection system may be used to measure the absence, presence, and amount of hybridization for all of the distinct sequences simultaneously (e.g., Heller et al., Proc. Natl. Acad. Sci. 94:2150-2155, 1997). Preferably, a scanner is used to determine the levels and patterns of fluorescence.

Polypeptides and fragments thereof may be analyzed using compositions of the invention, Typically, such compositions feature a protein, or fragment thereof, bound to a solid support. Suitable solid supports include membranes (e.g., membranes composed of nitrocellulose, paper, or other material), polymer-based films (e.g., polystyrene), beads, or glass slides. For some applications, proteins are spotted on a substrate using any convenient method known to the skilled artisan (e.g., by hand or by inkjet printer). Preferably, such methods retain the biological activity or function of the protein bound to the substrate (Ge et al., supra; Zhu et al., supra).

A composition of the invention is hybridized with a detectable probe. Such probes can be polypeptide, nucleic acid, or small molecules. Probes can also include antibodies, candidate peptides, nucleic acids, or small molecule compounds derived from a peptide, nucleic acid molecule, or chemical library. Hybridization conditions (e.g., temperature, pH, protein concentration, and ionic strength) are optimized to promote specific interactions. Such conditions are known to the skilled artisan and are described, for example, in Harlow, E. and Lane, D., Using Antibodies: A Laboratory Manual. 1998, New York: Cold Spring Harbor Laboratories. After removal of non-specific probes, specifically bound probes are detected, for example, by fluorescence, enzyme activity (e.g., an enzyme-linked calorimetric assay), direct immunoassay, radiometric assay, or any other suitable detectable method known to the skilled artisan.

The surface of compositions of the invention may, for example, be ionic, anionic, hydrophobic; comprised of immobilized nickel or copper ions, comprised of a mixture of positive and negative ions; and/or comprised of one or more antibodies, single or double stranded nucleic acids, proteins, peptides or fragments thereof, amino acid probes, or phage display libraries. Many protein biochips are described in the art. These include, for example, protein biochips produced by Ciphergen Biosystems (Fremont, Calif.), Packard BioScience Company (Meriden Conn.), Zyomyx (Hayward, Calif.) and Phylos (Lexington, Mass.). Examples of such protein biochips are described in the following patents or patent applications: U.S. Pat. No. 6,225,047 (Hutchens and Yip, "Use of retentate chromatography to generate difference maps," May 1, 2001); International publication WO 99/51773 (Kuimelis and Wagner, "Addressable protein arrays," Oct. 14, 1999); U.S. Pat. No. 6,329,209 (Wagner et al., "Arrays of protein-capture agents and methods of use thereof," Dec. 11, 2001) and International publication WO 00/56934 (Englert et al., "Continuous porous matrix arrays," Sep. 28, 2000).

Analytes may be captured with capture reagents immobilized to a solid support, such as a biochip, a multiwell microtiter plate, a resin, or nitrocellulose membranes that are subsequently probed for the presence of analytes. Capture can be on a chromatographic surface or a biospecific surface. For example, a sample containing the analyte, such as a lysate obtained from a tissue sample, may be contacted with the active surface of a biochip for a sufficient time to allow binding. Then, unbound molecules are washed from the surface using a suitable eluant, such as phosphate buffered saline. In general, the more stringent the eluant, the more tightly the proteins must be bound to be retained after the wash.

Upon capture on a chip or other substrate, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry, and in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Mass spectrometry (MS) is a well-known tool for analyzing chemical compounds. Thus, in one embodiment, the methods of the present invention comprise performing quantitative MS to measure an analyte. The method may be performed in an automated (Villanueva, et al., *Nature Protocols* (2006) 1(2):880-891) or semi-automated format. This can be accomplished, for example with MS operably linked to a liquid chromatography device (LC-MS/MS or LC-MS) or gas chromatography device (GC-MS or GC-MS/MS). Methods for performing MS are known in the field and have been disclosed, for example, in US Patent Application Publication Nos: 20050023454; 20050035286; U.S. Pat. No. 5,800,979 and references disclosed therein.

The protein fragments, whether they are peptides derived from the main chain of the protein or are residues of a side-chain, are collected on the collection layer. They may then be analyzed by a spectroscopic method based on matrix-assisted laser desorption/ionization (MALDI) or electrospray ionization (ESI). The preferred procedure is MALDI with time of flight (TOF) analysis, known as MALDI-TOF MS. This involves forming a matrix on the membrane, e.g. as described in the literature, with an agent which absorbs the incident light strongly at the particular wavelength employed. The sample is excited by UV, or IR laser light into the vapour phase in the MALDI mass spectrometer. Ions are generated by the vaporization and form an ion plume. The ions are accelerated in an electric field and separated according to their time of travel along a given distance, giving a mass/charge (m/z) reading which is very accurate and sensitive. MALDI spectrometers are commercially available from PerSeptive Biosystems, Inc. (Frazingham, Mass., USA) and are described in the literature, e.g. M. Kussmann and P. Roepstorff, cited above.

Test Samples

Methods and compositions of the invention are useful for the identification of an analyte (e.g., chemical or biological in origin) in a test sample. In one embodiment, the methods of the invention are suitable for detecting analytes of biological origin. Test samples include, but are not limited to, any liquid containing a dissolved or dispersed analyte of biological origin. If the test sample is not in itself sufficiently fluid for the present purpose, it may be admixed with a suitable fluid to the desired fluidity, for instance by homogenization. In one example, a sample is homogenized in any suitable liquid to test for the presence of contaminants, such as pathogens or their toxins. Exemplary test samples include body fluids (e.g. blood, serum, plasma, amniotic fluid, sputum, urine, cerebrospinal fluid, lymph, tear fluid, feces, or gastric fluid), tissue extracts, culture media (e.g., a liquid in which a cell, such as a pathogen cell, has been grown), environmental samples, agricultural products or other foodstuffs, and their extracts. In one embodiment, a test device of the invention detects the presence of a pathogen in a sample. Exemplary pathogens include fungal, bacterial, or viral proteins or metabolites, including secondary metabolites, such as toxins, in a test sample. In another embodiment, a test device of the invention detects a peptide or protein. Exemplary proteins and polynucleotides include biomarkers whose differential expression is associated with disease. For environmental applications, test samples may include water, liquid extracts of air filters, soil samples, building materials (e.g., drywall, ceiling tiles, wall board, fabrics, wall paper, and floor coverings), environmental swabs, or any other sample suitable for use in a liquid assay.

Diagnostics

Expression levels of particular nucleic acids or polypeptides may be correlated with a particular disease state, and thus are useful in diagnosis. The present invention provides compositions and methods having increased accuracy and reproducibility for detecting analytes in a sample relative to conventional diagnostics. In one embodiment, a patient having a disease will show an alteration in the expression of a polypeptide or polynucleotide. Alterations in gene or polypeptide expression are detected using methods known to the skilled artisan and described herein. In other embodiment of the methods of the invention, multiple markers are measured in a single assay. The use of multiple markers increases the predictive value of the test and provides greater utility in diagnosis, toxicology, patient stratification and patient monitoring. The process detects expression profiles formed by the analysis of multiple markers. Such analysis may improve the sensitivity and specificity of clinical proteomics for predictive medicine. Subtle variations in data from clinical samples indicate that certain patterns of protein expression can predict phenotypes such as the presence or absence of a certain disease, a particular stage of disease progression, or a positive or adverse response to drug treatments.

Data generated by detection of markers can be analyzed using any suitable means. In one embodiment, data is analyzed with the use of a programmable digital computer. The computer program generally contains a readable medium that stores data. This data can indicate the number of analytes detected, including the strength of the signal generated by each analyte. Data analysis can include the steps of determining signal strength of a analyte detected. When the sample is measured and data is generated, the data is then analyzed by a computer software program.

As indicated above, the invention provides methods for aiding a human disease diagnosis using one or more compositions, as specified herein. The compositions and methods of the invention detect analytes that are differentially present in samples of a subject having or having a propensity to develop a disease and a normal subject in whom such disease is undetectable. For example, some of the analyte (e.g., polypeptides, polynucleotides) are expressed at an elevated level and/or are present at a higher frequency in diseased subjects than in normal subjects, while some of the analyte are expressed at a decreased level and/or are present at a lower frequency in diseased subjects than in normal subjects. Therefore, detection of one or more analytes in a person would provide useful information regarding the probability that the person may have a disease.

Kits

The invention provides kits that include a test device for the detection of an analyte in a sample. In some embodiments, the kit comprises a container, which contains a composition of the invention (e.g., microarray, beads, or other substrate comprising a capture agent); such containers can be boxes, ampoules, bottles, vials, tubes, bags, pouches, blister packs, or other suitable container forms known in the art. In one embodiment, such containers may be sterile. Such containers can be made of plastic, glass, laminated paper, metal foil, or other materials suitable for holding medicaments.

If desired the device is provided together with instructions for using it to identify the presence or absence of an analyte in a sample. The instructions will generally include information about the use of the device for the identification of a particular analyte, such as an antigen in a liquid sample (e.g., a environmental sample, biological sample, or liquid sample extracted from an agricultural commodity). The instructions may be printed directly on the container (when present), or as a label applied to the container, or as a separate sheet, pamphlet, card, or folder supplied in or with the container. If desired, the kit may also include a standard measure pipet, a test vial, and/or a liquid (e.g., ethanol, methanol, organic solvent, suitable buffer, such as phosphate buffered saline, or water) to be used in the extraction of a sample.

Methods of Analyzing Microarrays

Referring now to FIG. 9, a method 900 of analyzing a microarray is provided.

In step S902, a substrate is provided. The substrate can be a substrate as described herein, for example, a substrate having a plurality of replicates for each of a plurality of coupling concentration levels of a capturing agent. In a specific embodiment, the substrate has M×N units, wherein M detection units of the substrate are replicates for each of N amounts of a capturing agent.

In step S904, specimen is introduced to the substrate. The sample can include or can potentially include one or more target analytes as discussed herein.

In step S906, the substrate is imaged. The substrate can be imaged in accordance with a variety of technologies and protocols as described herein. For example, the substrate can be imaged with a camera such as a charge-coupled device (CCD). One or more filters can be used to filter or condition light entering the camera, thereby allowing the camera to better image wavelengths of interest (e.g., fluorescent wavelengths).

Imaging step S906 can include extracting data from the imaged substrate. For example, individual detection units can be identified within the image using existing image processing software. Data (e.g., wavelength, intensity, coupling concentration levels, and the like) can be extracted for each detection unit.

In step S908, a proportion of positive detection units is computed for each amount of capturing agent. A positive unit can be any unit that exhibits a response exceeding a defined threshold. The defined threshold can be a user-defined threshold and can vary between assays. For example, the defined threshold can be the intensity and/or wavelength of light (e.g., fluorescent light) emitted from a detection unit. The concentration level can be denoted as $b(i)$, $i=1, 2, \ldots, N$. The proportion of positive units can be denoted as $x(i)$ and expressed as $$x(i) = \frac{m(i)}{M},$$

wherein $m(i)$ is the number of positive units for coupling concentration level $b(i)$.

Step S908 can optionally include removing outliers. For example, detection units having exceptionally high or low values can be discarded in accordance with standard statistical and laboratory protocols.

In step S910, each of the proportions of positive detection units can be associated with its corresponding amount of capturing agent. For example, proportions and capturing agent levels can be stored as pairs (x(i), b(i)) for i=1, 2, . . . , N.

In step S912, the associated proportions of positive units and capturing agent levels can be used to quantify a concentration of a target analyte.

In step S912a, the amount of the target analyte can be quantified by fitting a curve f(b) to the associated proportions of positive detection units and capturing agent levels. Curve f(b) can be a parametric curve.

Various curves can be selected to reflect various substrates, assays, target analytes, and the like. For example, to analyze the data of a competitive immunoassay, the parametric curve f(b) can be a truncated sigmoid function with four parameters A(1), A(2), A(3), and A(4), wherein $$f(b) = \begin{cases} y - A(4) & \text{if } y > A(4) \\ 0 & \text{else} \end{cases}$$

and wherein $$y = \frac{A(3)}{1 + e^{A(1)X + A(2)}}$$

In step S912b, the parameters of the fitted curve can be used to compute a value h such that f(h) equals a constant k. Constant k can be an arbitrary unit (e.g., 0.5) that allows for quantification and comparison of the abundance of an analyte in the specimen.

Referring now to FIG. 10, another method 1000 of analyzing a substrate is provided.

In step S1002, a substrate is provided. The substrate can be a substrate as described herein, for example, a substrate having a plurality of replicates for each of a plurality of amounts of a capturing agent. In a specific embodiment, the substrate has M×N units, wherein M units of the substrate are replicates for each of N amounts of a capturing agent.

In step S1004, specimen is introduced to the substrate. The sample can include or can potentially include one or more target analytes as discussed herein.

In step S1006, the substrate is imaged. The substrate can be imaged in accordance with a variety of technologies and protocols as described herein. For example, the substrate can be imaged with a camera such as a charge-coupled device (CCD). One or more filters can be used to filter or condition light entering the camera, thereby allowing the camera to better image wavelengths of interest (e.g., fluorescent wavelengths).

Imaging step S1006 can include extracting data from the imaged substrate. For example, individual units can be identified within the image using existing image processing software. Data (e.g., wavelength, intensity, coupling concentration levels, and the like) can be extracted for each detection unit.

In step S1008, one or more bootstrapping iterations are performed. Each iteration includes selecting one or more responses from each of the capturing agent levels (step S1008a), fitting the selected responses to a curve (step S1008b), and calculating an y-intercept for a linear portion of the curve (step S1008c). For each bootstrap iteration r, a fixed number of K units can be selected at each of the N capturing agent levels to form a random resample (x(i,k), b(i,k)) for k=1, 2, . . . , K and I=1, 2, . . . , N.

In step S1010, a mean of the y-intercepts is calculated.

The above method 1000 can be also used to derive an algorithm for analyzing a substrate. In such a method, step S1006 is performed for data separate from the test data (and, therefore, is not a bootstrapping iteration). Once one or more curves are fitted, the one or more curves can be provided (e.g., in software) along with a substrate as part of a kit as described herein.

Curve Fitting

The methods described herein, particularly the functional forms of the parameterized curves for data fitting, are dependent on how the multiple concentration levels of the capturing agent are spaced along a gradient. The use of log-log transformation and the particular functional form of the fitting curved used in algorithm #2 in general works well when the concentrations of the capturing agent are spaced in exponential scale along a gradient. For example, in one experiment, the units in the array-based assay were spotted with capturing agent TRIM21 antigen in the exponential scale gradient of {0.40 ng/ul, 0.80 ng/ul, 1.60 ng/ul, . . . , 200.00 ng/ul, 400.00 ng/ul}. With logarithmic transformation, the gradient becomes in linear scale, which permits the use of a simpler functional form for curve fitting.

There are be many different ways to decide on a particular gradient for the capturing agent, for biological or biochemical reasons, or for experimental procedural reason. For example, the choice of exponential scale gradient was the relatively efficiency and better quality control in diluting the capturing agents in multiple of 2's in comparison to diluting the solution in precise linear intervals.

During the assay development stage, it is in general necessary to test an assay with an overly large number of capturing agent concentration levels with a broad coverage and a sufficiently large number of replicate units per concentration level. The assay will then be tested on samples representative of the actual application, including coverage of extreme cases of target analyte abundances. Data generated from such experiment will be used through statistical and computational approaches to determine the optimal range of capturing agent concentration and the minimal number of concentration levels and minimal number of units per concentration level that provide the required performance for the assay.

The same data, however, even before being used for the selection of concentration levels and number of units, can be used to assist in determining the functional forms of the fitting curves and deriving steps of the algorithm that converts the data from capturing units to a single value quantity representative of the abundance of the target analyte in specimen. In general, the intensity data from the capturing units is plotted against their known coupling capturing agent concentration levels. From such plot, one can decide whether any data preprocessing including transformation is required to facilitate the curve fitting process. One can also decide on the simplest functional forms (i.e., the functional forms having the least number of parameters) that would fit the data well. Attention should be made to ensure that the function form will not "amplify" variations in data due specific mathematical formula or computational steps. It is possible that a number of functions with equal simplicity would perform equally well for practical purposes.

Implementation of Methods in Hardware and/or Software

As will be appreciated by one of ordinary skill in the art, the methods described herein can be implemented in hardware and/or software. For example, a general purpose computer can execute a software program that implements the methods described herein, thereby becoming a speciallyprogrammed computer configured to implement the methods herein. Such a computer can include a processor for performing the methods described herein and communication interfaces for receiving data from an data source (e.g., memory, an imaging device, another computer, and the like), receiving instructions (e.g., a keyboard, a mouse, a touch screen, and the like), and communication results (e.g., a monitor, a printer, and the like).

Software implementing the methods herein can be stored in computer-readable media for execution on a computer. Such computer-readable media can be tangible or intangible and can be transitory or non-transitory.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

The following examples are put forth so as to provide those of ordinary skill in the art with a complete disclosure and description of how to make and use the assay, screening, and therapeutic methods of the invention, and are not intended to limit the scope of what the inventors regard as their invention.

Example 1

Simulation Using Immunoassay Models

In one embodiment, a simulation is used to demonstrate the effectiveness of the reported assay design and the computational approaches to achieve a high level of analytical performance that overcomes the analytical variability that is inherently present in assay production and application. In one example, a simulated affinity capturing array was generated, wherein the capturing agent was coupled at N=96 concentration levels in equal linear intervals and with M=48 units as replicates at each of the concentration levels. To simulate analytical variability in array production, the actual coupling concentrations for individual spots in an array were corrupted by a zero-mean normally distributed noise with a variance that effectively introduced an analytical variability of 30% CV (coefficient of variation) to array production (FIG. 4A).

In an array application, the noise-corrupted arrays were processed with two samples having different concentrations of the target analyte. The detected analog signal from affinity capturing was computed based on the competitive immunoassay model (Campfield, 1983; Chan, 1987). The array processing and signal detection process were in combination further corrupted with an additional zero-mean normally distributed noise, which resulted in an equivalent additional analytical variance of 30% CV.

Example 2

Experimental Arrays Using New Design

To experimentally verify the effectiveness of the new design of high-density assays, we spotted arrays (1"×3" nitrocellulose coated-glass slides) with purified human protein TRIM21 (tripartite motif-containing 21) using a contact-type printer and used the arrays to test pooled human serum from patients with lupus and other autoimmune diseases with known elevation of auto-antibodies to TRIM21. The TRIM21 antigen was diluted into 96 concentration levels ranging from 0.40 ng/ul to 400.00 ng/ul at equal intervals in logarithmic scale. The dilutions were divided 4 times and placed in a 384-well plate and used for array printing. Each well was used to print 10 spots, which resulted in the equivalent of 40 replicates for each TRIM21 concentration level. Additional positive and negative control proteins, such as human IgG and BSA were also printed at varying concentration levels within each block on the arrays.

The printed arrays after passing quality control procedures were then processed with the pooled patient serum samples. Two sets of experiments were done. In the first experiment, the serum samples were diluted at ×200, ×400, ×800, and ×1600. In the second experiment, the dilutions were ×150, ×300, ×600, ×1200, and ×2400.

After blocking the arrays with blocking buffer at 4 C for 2 hour with mixing, the arrays were incubated with a washing buffer and then were incubated with serial diluted serum samples for 1 hour at 4 C with mixing. Following this incubation, the arrays were washed for 3 times×10 minutes with washing buffer. The arrays were then incubated with diluted anti-human AlexaFluor conjugate solution in 1000× washing buffer for 90 minutes at 4 C with mixing. Wash for another 3 times with washing buffer and twice with deionized water. The arrays were dried by centrifuging at a low speed (500 rpm) for 5 minutes and then scanned using a GenePix4000B microarray scanner. The GenePix software system was used to extract and convert the scanned images into numerical readouts as the detected signals for the individual affinity-capturing units (spots).

Example 3

Computational Algorithms

The rich content in data from the new design of high-density affinity-capturing assays inspired a number of interesting computational algorithms aimed at two important aspects of assay development: 1) to reduce the impact of analytical variability in assay production and application to the final assay results, and 2) to expand the overall dynamic range of the assay. The first algorithm was used in analyzing data from the simulated immunoassay. The second algorithm was used to analyze the experimental data from the TRIM21 arrays. One of skill in the art can adjust the form and parameters of the fitting curves according to how the gradient of the capturing agent concentration levels are spaced between adjacent levels. Concentration levels are spaced linearly, non-linearly, and/or exponentially. Exemplary spacing include the following: 10 ng/ml, 15 ng/ml, 20 ng/ml (linear); 1 ng, 2 ng, 4 ng, (doubling); exponential scale, or any other desired format.

In addition to the use of the GenePix software system, prior to the application of the following algorithms, the extracted array data were further preprocessed to identify spatially adjacent spots that were of poor quality due to either defects in array production or uncontrolled variations in array processing. Data from the affected units were excluded from further analysis. With the large number of replicates, such exclusion, in general, did not affect the overall data analysis process.

Algorithm #1:

For a high-density assay of N×M units where M units are used as replicates for each of the N coupling concentration levels of the capturing agent.
1. Select a predetermined or computationally calculated cutoff value and use it to convert the numerical readout values of individual capturing units to the binary value of 1 (positive) or 0 (negative).
2. For each capturing agent couple concentration level $b(i)$, $i=1, 2, \ldots, N$, compute the proportion of positive units $x(i)=m(i)/M$, where $m(i)$ is the number of units reported positive at coupling concentration level $b(i)$ (FIG. 2C). An optional procedure may be used to remove outliers in computing the proportion of positive units.
3. The sequence of pairs $\{(x(i), b(i)), i=1, 2, \ldots, N\}$ is then used to quantify the concentration of target analyte in the sample (FIG. 3). As an example, to analyze the simulated array data of a competitive immunoassay, the parametric curve f(b) representing a truncated sigmoid function with four parameters A(1), A(2), A(3), and A(4) was used to fit the data: $f(b)=y-A(4)$ if $y>A(4)$, else $f(b)=0$, where $y=A(3)/(1+\exp(A(1)*X+A(2)))$.
4. Finally, the parameters of the fitted curve are used to compute a value h defined as the horizontal distance between $f(h)=0.5$ and the origin (FIG. 3A). h was used as a quantitative measure (of arbitrary unit) for the abundance of analyte in specimen (FIG. 3B)

Figure 1A:
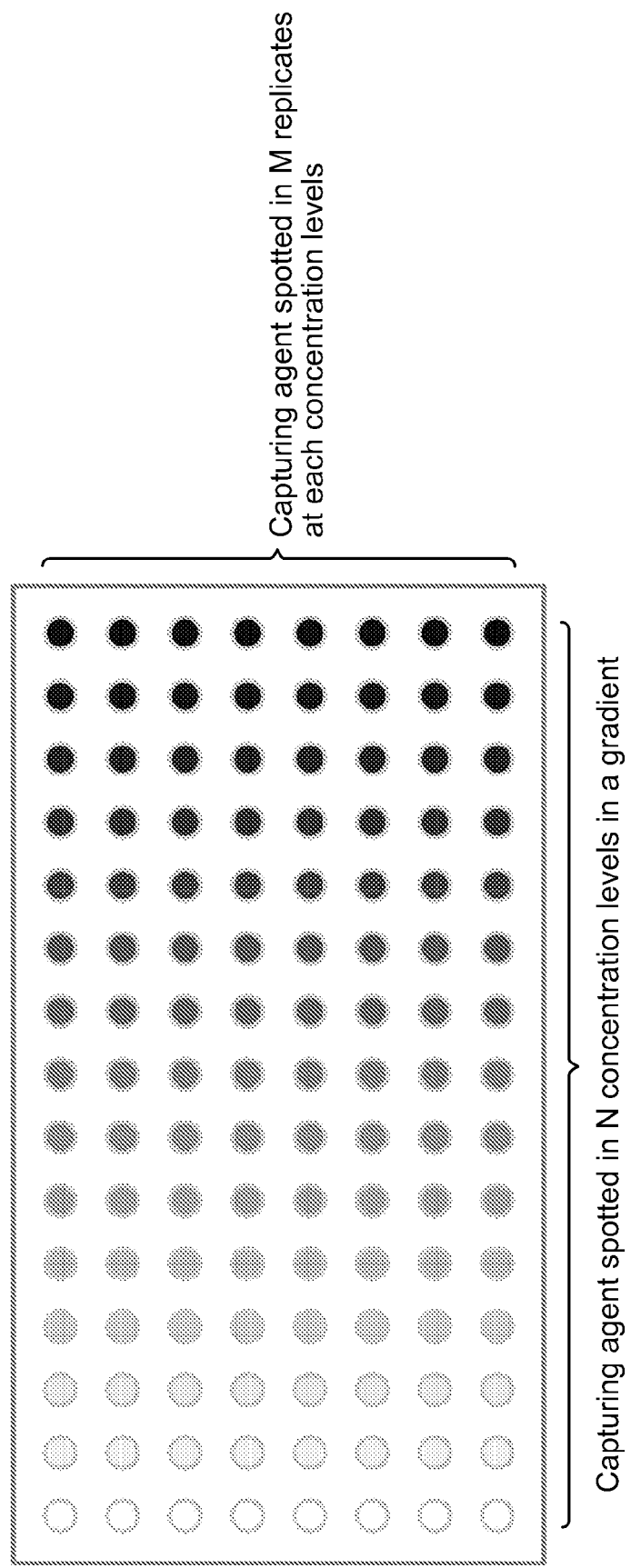
FIGS. 1A-1E are schematic diagrams that provide a small scale example to illustrate the design of assay (FIG. 1A), the processing of an assay using a given specimen (FIG. 1B), the conversion of individual unit readouts to binary values and the calculation of proportion of positive units for each capturing agent concentration level (FIG. 1C), and the fitting of data to a parameterized curve (FIG. 1D). When the arrays are used for specimens with a higher/lower abundance of the target analyte, there will be more/less units having positive signals and the fitted curve will shift towards the left or right (FIG. 1E).
Figure 1B:
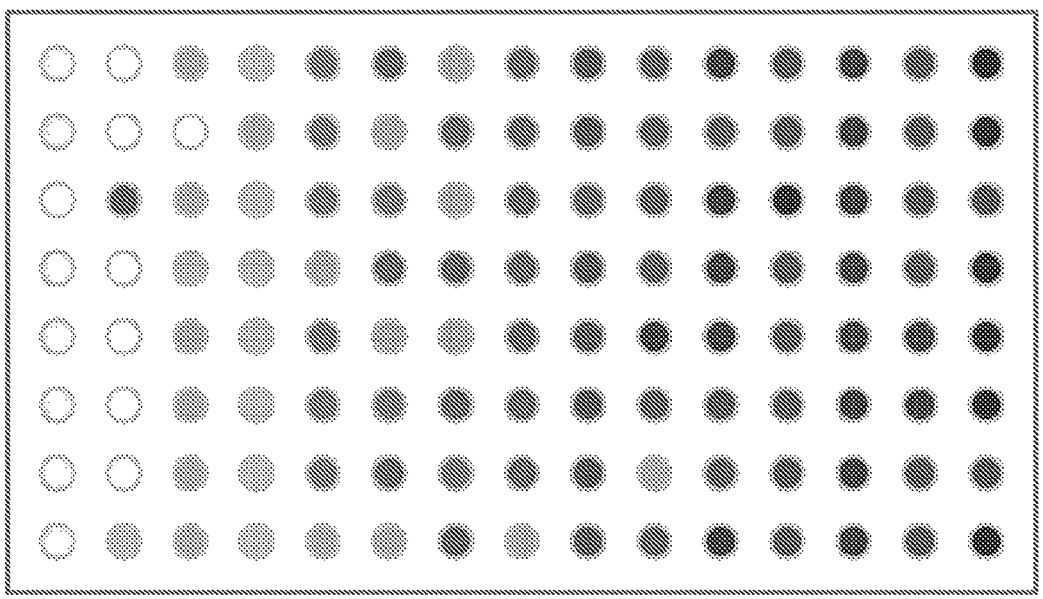
Figure 1C:
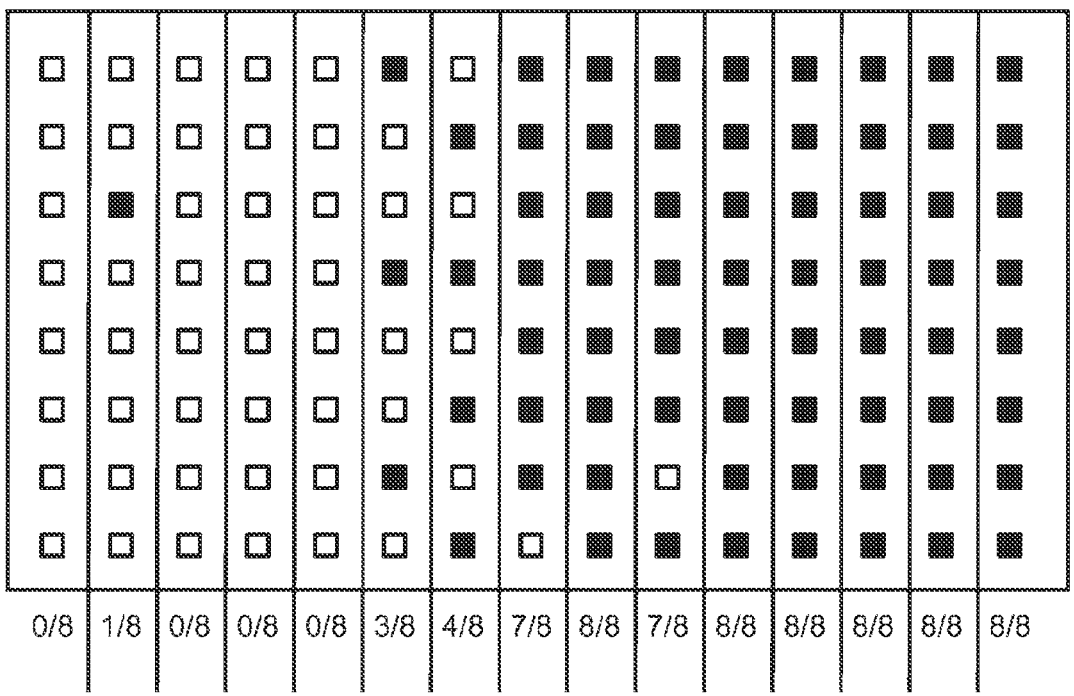
Figure 1D:
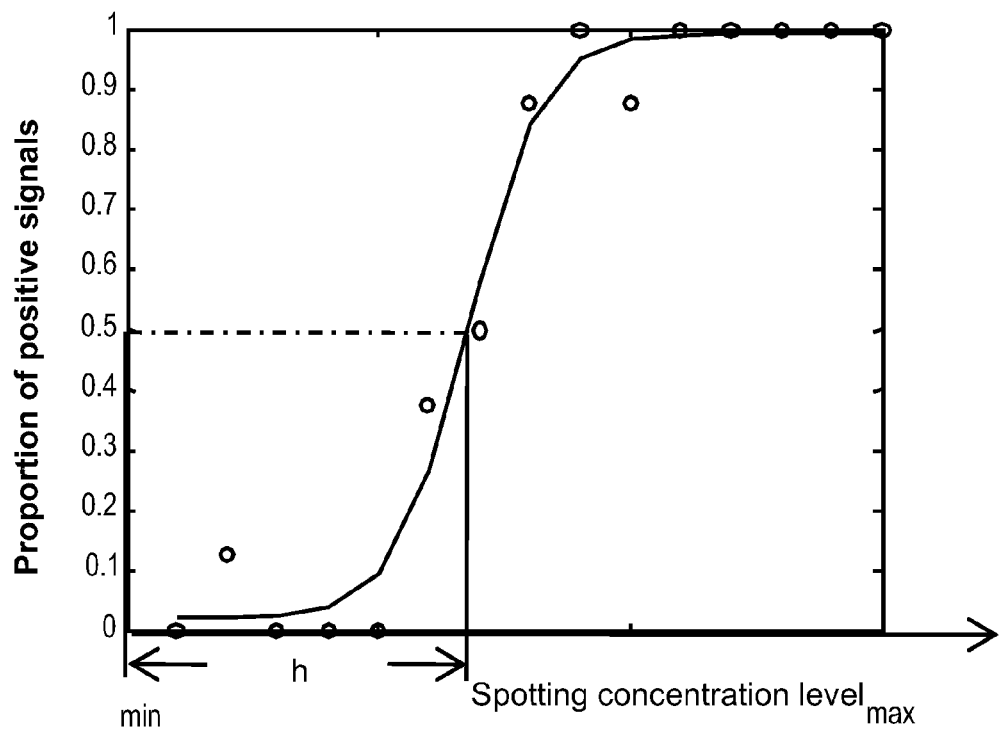
Figure 1E:
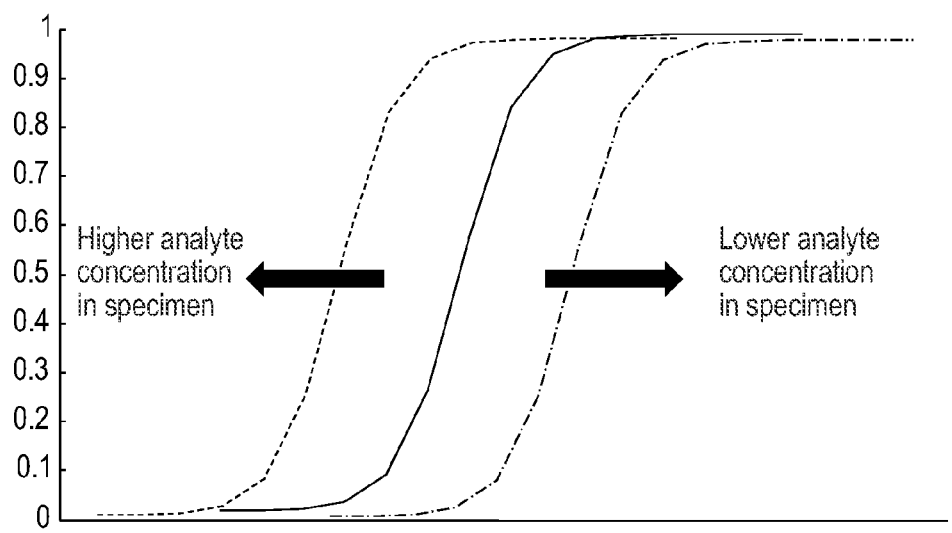

FIGS. 1 A-E provide a schematic representation of a small scale example to illustrate the design of assay (FIG. 1A), the processing of an assay using a given specimen (FIG. 1B), the conversion of individual unit readouts to binary values and the calculation of proportion of positive units for each capturing agent concentration level (FIG. 1C), and the fitting of data to a parameterized curve (FIG. 1D). Note that when the arrays are used for specimens with a higher/lower abundance of the target analyte, there will be more/less units having positive signals and the fitted curve will shift towards the left/right (FIG. 1E).

Algorithm #2:

In the second algorithm, instead of converting to binary values, data from individual units at each capturing agent concentration level, after preprocessing and removal of outliers, were used directly in a bootstrap algorithm to estimate the abundance of target analyte in the specimen by aggregating information from multiple replicates and from all capturing agent coupling concentration levels.
1. For bootstrap run r, randomly select fixed number of K units at each of the N capturing agent coupling concentration levels to form a random resample $\{(x(i,k), b(i,k)), k=1, 2, \ldots, K, i=1, 2, \ldots, N\}$.
2. Transform the data from units in the random resample into log-log scale $\{(xhat(i,k), bhat(i,k)), k=1, 2, \ldots, K, i=1, 2, \ldots, N\}$, where $xhat(i,k)=\log(x(i,k))$ and $bhat(i,k)=\log(b(i,k))$. The data are used to fit the following curve: $f(bhat)=A(1)*(xhat(i)+A(2))$ if $xhat<A(3)$, and $f(bhat)=A(1)*A(3)+A(2)$ if $xhat>=A(3)$.
3. Save $h(r)=A(2)$, which is the intercept of the linear portion of the fitted curve.
4. Repeat steps 1-3 for a prefix number of bootstrap runs.
5. Estimate the abundance of target analyte in specimen: h value=mean(h(r)).

Computational Approaches for Selecting Capturing Agent Coupling Concentration Levels and Number of Replicate Units.

The number of concentration gradient levels N should be chosen such that it provides a sufficient quantification resolution in measurement required by the application. Furthermore, the lower and upper bounds of the concentration gradient levels should be chosen such that the affinity-capturing signals sufficiently covers the dynamic range of the corresponding target analyte in the specimen as required by the application. The number of replicates M at each concentration level should also be chosen such that a desired level of quantification precision in measurement can be reached through statistically-principled calculations, such as the abovementioned algorithms. In practice, the high-density nature of assays make it possible during the assay development stage to use both an excessive number of capturing agent concentration levels with extreme lower and upper concentration limits and an excessive number of replicate units for each level. The resultant data will allow the application of computational approaches and statistical re-sampling methods to determine the appropriate assay design with parameters such as the lower and upper concentration limits for the capturing agent and the minimum number of concentration levels and number of replicate units needed to achieve an acceptable performance for a particular application. Designs for individual assays, with additional development work, can then become potentially portable onto a single high-density multiplexed assay.

Example 4

Simulation Using Competitive Immunoassay Model

FIG. 2 shows the simulation results using the competitive immunoassay model. A column in the image corresponds to replicate units (M=48) of the same capturing agent concentration level while a row in the image represents units (N=96) printed with capturing agent in a discrete gradient. In actual experiments, the capturing units are to be printed with randomized spatial patterns to eliminate analytical variability being confounded with expected signals from units. The figures can be viewed as images of detected signals rearranged by capturing agent concentration levels.

FIG. 2A shows the array design with and without corruption of zero-mean Gaussian noise and variability in array printing that corresponds to a CV of 30%, respectively. FIG. 2B compares the simulation results of the array processed using two specimens of different levels of the target analyte. An additional zero-mean Gaussian noise, also corresponding to a CV of 30%, was added during the array processing and scanning procedures. FIG. 2C provides images of arrays after conversion of unit data into binary values. FIG. 2D plots the results of curve-fitting using the two arrays' simulated data. Finally, FIG. 2E includes fitted curves using arrays processed with specimens of low (left), medium (middle), and high (right) analyte concentrations.

Using a computer simulation, samples having varying amounts of a target analyte were applied to an array. The resulted fitted curves were plotted in FIG. 3A, which also demonstrate how the distance h was measured for each of the curves. In FIG. 3B, the h values were plotted against the known analyte concentrations in the samples, demonstrating a smooth response curve over the entire analyte concentration range. The CVs of h values were estimated by repeating the above simulation procedures 20 times. In FIG. 3C, the maximum CV was <4% even though both the array printing and processing had each been subjected to an added variability of 30% CV.

Example 5

Selection of Number of Levels in Capturing Agent Concentration Gradient and Number of Replicate Units Per Concentration Level The data generated from two experiments using arrays of the new design spotted with TRIM21 antigens allowed us to test computationally the effect of a reduction in the number of concentration levels for the capturing agent and the number of units used for each of the concentration levels. The results indicated that the estimated h values were remarkably stable. When the number of replicate units per concentration level were reduced from 40 to less than 10 there was no noticeable increase in CVs across all sample dilutions (CVs=3.8%, 7.0%, 5.5%, 8.3%, and 6.3% for the 5 dilution levels, respectively). Similar stability was observed with the reduction of discrete levels in the concentration gradient. However, as the number of concentration level was reduced, the response curve became flat for sample dilutions above ×1200, indicating the assay started to have a higher limit of detection (FIG. 7).

Example 6

Results of Experimental Arrays Using the New Design

FIG. 4 plots in log-log scale the median signal intensities estimated using the M=40 replicate units at the known spotting concentration levels of TRIM21 antigen based on data from arrays processed with pooled human sera at ×200, ×400, ×800, and ×1600 dilutions. The experimental data demonstrated good concentration-dependent responses with an overall CV of 1.0%, 1.6%, 6.0%, and 6.0%, correspondingly. Shown in FIG. 5 are the estimated h values by Algorithm #2 plotted against the dilution rate of the pooled patient serum proportional to the descending abundance of TRIM21 autoantibodies in samples.

The invention provides a composition for quantitating one or more analytes in a sample. a novel design of high-density assays that uses a large number of relatively low quality affinity-capturing units and computational algorithms to achieve a level of analytical performance that makes it potentially applicable to demanding applications such as clinical laboratory testing. The scalable nature of this design allows one to generate sufficient data through a small number of experiments and then use computational algorithms to refine a final and efficient design. This can potentially lead to the rapid development of multiplexed assays. The capturing units in such assays are not restricted to spots in arrays or beads. The design can be applied to help improve performance of any technologies that can be viewed in abstraction as comprised of a large number of sensory units.

Due to the relatively low performance quality of individual units, a unit's dynamic range in its response curve will often be very small. The use of units coupled with capturing agents in a gradient makes it possible to computationally overlap multiple small response curves to create an overall response curve that has an expansive dynamic range as illustrated in FIG. 8.

Furthermore, it is expected that for any given abundance level of a target analyte in specimen, there will be at least some among the many units of different capturing agent concentrations that are at their affinity-capturing "sweet-spots" and hence provide reliable and reproducible signals. Data from these units will anchor the statistical/computational algorithms used to estimate the h values. As a result, statistical estimation made using the collective data from replicate units of varying capturing agent concentrations will more likely to have better stability than estimation made by units of a single capturing agent concentration only.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method for determining the abundance of one or more target analytes in a sample, the method comprising:
   a) contacting a target analyte with a set of detection units for each analyte fixed to a rectangular substrate in an array format, wherein each detection unit comprises a discrete amount of a capture agent capable of specifically binding the target analyte, and the amount of capturing agent varies over the set to form an exponential concentration gradient, under conditions that allow binding of the target analyte to the capture agent, wherein the set of detection units comprises multiple replicates for any single concentration level of any single capturing agent, such that the CV (coefficient of variation) is less than 4% for detection of the target analyte concentration in the sample,
   b) detecting binding of the target analyte to the capture agent, and
   c) determining the amount of target analyte present in the sample, wherein said step of determining comprises logarithmic transformation and curve fitting.

2. The method of claim 1, wherein the number of detection units present in the set is sufficient to provide a quantitative read-out of the abundance of the target analyte in the sample based on the aggregation of data of an analyte detected by the individual detection units.

3. The method of claim 1, wherein the set of detection units for each analyte is a microarray, a collection of beads, a 2-dimensional surface, a 3-dimensional surface, or other 2 dimensional or 3-dimensional shape that supports the immobilization of a capture agent by a detection unit.

4. The method of claim 1, wherein the detection unit is a spot of capture reagent present on a microarray, a single bead, a 2-dimensional surface, a 3-dimensional surface, or other 2 dimensional or 3-dimensional shape that supports the immobilization of a capture agent by a detection unit.

5. The method of claim 1, wherein the capture agent is a small compound, a polypeptide, a polynucleotide, a natural or synthetic particle.

6. The method of claim 5, wherein the small compound is organic, inorganic, biotin, or any other chemical compound.

7. The method of claim 1, wherein the capture agent is a polypeptide or fragment thereof comprising a detectable moiety.

8. The method of claim 7, wherein the polypeptide is an antibody or fragment thereof.

9. The method of claim 1, wherein said determining step c) comprises for each detection unit, computing a proportion of positive detection units.

10. The method of claim 9, wherein determining step (c) includes fitting a curve f(b) to the associated proportions of positive detection units and capture agent amounts.

11. The method of claim 10, further comprising:
utilizing the curve to compute a value h, wherein f(h) equals a constant k.

12. The method of claim 11, wherein k=0.5.

13. The method of claim 1, wherein said determining step c) comprises:
performing one or more bootstrapping iterations, each iteration comprising:
selecting one or more responses from each of the capture agent amounts;
fitting the selected responses to a curve; and
calculating a y-intercept for a linear portion of the curve; and
calculating a mean of the y-intercepts.

\* \* \* \* \*